US009791442B2

(12) United States Patent
Monteleone et al.

(10) Patent No.: US 9,791,442 B2
(45) Date of Patent: Oct. 17, 2017

(54) METHODS OF MONITORING RESPONSIVENESS TO ANTI-SMAD7 THERAPY

(75) Inventors: Giovanni Monteleone, Grottaferrata (IT); Francesca Viti, Salorino (CH); Salvatore Bellinvia, Balerna (CH)

(73) Assignee: Nogra Pharma Limited, Dublin (IE)

( * ) Notice: Subject to any disclaimer, the term of this patent is extended or adjusted under 35 U.S.C. 154(b) by 442 days.

(21) Appl. No.: 14/344,969

(22) PCT Filed: Sep. 14, 2012

(86) PCT No.: PCT/EP2012/068146
§ 371 (c)(1),
(2), (4) Date: Dec. 8, 2014

(87) PCT Pub. No.: WO2013/037970
PCT Pub. Date: Mar. 21, 2013

(65) Prior Publication Data
US 2015/0148245 A1 May 28, 2015

Related U.S. Application Data

(60) Provisional application No. 61/576,556, filed on Dec. 16, 2011.

(30) Foreign Application Priority Data

Sep. 15, 2011 (EP) .................... 11425234

(51) Int. Cl.
*G01N 33/569* (2006.01)
*G01N 33/68* (2006.01)
*G01N 33/50* (2006.01)

(52) U.S. Cl.
CPC ..... *G01N 33/56972* (2013.01); *G01N 33/505* (2013.01); *G01N 33/5094* (2013.01);
(Continued)

(58) Field of Classification Search
CPC ......... G01N 33/56972; G01N 33/6866; G01N 33/6869; G01N 33/6872; G01N 33/505;
(Continued)

(56) References Cited

U.S. PATENT DOCUMENTS 6,159,697 A  12/2000  Monia et al.
7,700,572 B2  4/2010  Steinbrecher et al.
(Continued)

FOREIGN PATENT DOCUMENTS

JP  2010-051307 A  3/2010
WO  WO-2004/087920 A1  10/2004
(Continued)

OTHER PUBLICATIONS

Best WR et al., (1976), 'Development of Crohn's Disease Activity Index. National Cooperative Crohn's Disease Study,' Gastroenterology, 70(3):439-44.
(Continued)

*Primary Examiner* — Jeremy C Flinders
(74) *Attorney, Agent, or Firm* — Goodwin Procter LLP

(57) ABSTRACT

Methods for monitoring whether a subject will be sensitive or resistant to treatment with an anti-SMAD7 therapy are disclosed. The methods are based on the determining of the amount of CCR9+ FOXP3+ T cells, CCR9+ IFN-gamma+ T cells, CCR9+ IL17A+ T cells, FOXP3+ T cells, IFN-gamma+ T cells, and/or IL17A+ T cells in a sample from the subject. Measurement of T cell populations may be determined by flow cytometry, immunohistochemistry, and/or ELISA.

24 Claims, 7 Drawing Sheets

(52) U.S. Cl.
CPC ..... *G01N 33/6866* (2013.01); *G01N 33/6869* (2013.01); *G01N 33/6872* (2013.01); *G01N 2333/54* (2013.01); *G01N 2333/7158* (2013.01); *G01N 2800/065* (2013.01); *G01N 2800/52* (2013.01)

(58) Field of Classification Search
CPC ....... G01N 33/5094; G01N 2333/7158; G01N 2333/54; G01N 2800/065; G01N 2800/52
See application file for complete search history.

(56) References Cited

U.S. PATENT DOCUMENTS

| | | | |
|---|---|---|---|
| 7,700,757 | B2 | 4/2010 | Monteleone |
| 7,807,818 | B2 | 10/2010 | Monteleone |
| 8,106,182 | B2 | 1/2012 | Monteleone |
| 8,648,186 | B2 | 2/2014 | Monteleone |
| 8,766,034 | B2 | 7/2014 | Shih et al. |
| 8,907,078 | B2 | 12/2014 | Monteleone |
| 8,912,154 | B2 | 12/2014 | Baroni et al. |
| 9,006,418 | B2 | 4/2015 | Monteleone |
| 9,096,854 | B1 | 8/2015 | Monteleone |
| 9,279,126 | B2 | 3/2016 | Monteleone |
| 9,314,434 | B2 | 4/2016 | Baroni et al. |
| 9,382,541 | B2 | 7/2016 | Monteleone |
| 9,499,819 | B2 | 11/2016 | Baroni et al. |
| 9,518,264 | B2 | 12/2016 | Monteleone |
| 9,605,264 | B2 | 3/2017 | Monteleone |
| 2005/0119203 | A1 | 6/2005 | Steinbrecher et al. |
| 2007/0042985 | A1 | 2/2007 | Monteleone |
| 2007/0167385 | A1 | 7/2007 | Monteleone |
| 2009/0156539 | A1 | 6/2009 | Monteleone |
| 2009/0275496 | A1 | 11/2009 | Baldwin et al. |
| 2010/0317719 | A1 | 12/2010 | Monteleone |
| 2011/0008795 | A1 | 1/2011 | Ikeda et al. |
| 2011/0207795 | A1 | 8/2011 | Steinbrecher et al. |
| 2012/0015033 | A1 | 1/2012 | Baroni et al. |
| 2012/0079611 | A1 | 3/2012 | Shih et al. |
| 2012/0136043 | A1 | 5/2012 | Monteleone |
| 2014/0142163 | A1 | 5/2014 | Monteleone |
| 2014/0256788 | A1 | 9/2014 | Monteleone |
| 2014/0271860 | A1 | 9/2014 | Monteleone et al. |
| 2015/0125523 | A1 | 5/2015 | Baroni et al. |
| 2015/0211011 | A1 | 7/2015 | Monteleone |
| 2015/0218561 | A1 | 8/2015 | Monteleone |
| 2015/0232854 | A1 | 8/2015 | Baroni et al. |
| 2015/0315573 | A1 | 11/2015 | Monteleone et al. |
| 2015/0337312 | A1 | 11/2015 | Monteleone |
| 2016/0177306 | A1 | 6/2016 | Monteleone |
| 2016/0222383 | A1 | 8/2016 | Baroni et al. |
| 2016/0304876 | A1 | 10/2016 | Monteleone |
| 2017/0107520 | A1 | 4/2017 | Baroni et al. |

FOREIGN PATENT DOCUMENTS

| | | |
|---|---|---|
| WO | WO-2007/014420 A1 | 2/2007 |
| WO | WO-2008/157394 A2 | 12/2008 |
| WO | WO-2010/054826 A1 | 5/2010 |
| WO | WO-2011/003905 A1 | 1/2011 |
| WO | WO-2013/158868 A1 | 10/2013 |
| WO | WO-2014/140333 A1 | 9/2014 |
| WO | WO-2015/169966 A2 | 11/2015 |
| WO | WO-2016/059239 A1 | 4/2016 |
| WO | WO-2016/059243 A2 | 4/2016 |
| WO | WO-2017/055611 A2 | 4/2017 |

OTHER PUBLICATIONS

Boirivant M et al., (2006), 'Inhibition of Smad7 with a Specific Antisense Oligonucleotide Facilitates TGF-α1-Mediated Suppression of Colitis,' Gastroenterology, 131(6):1786-98.

Fantini MC et al., (2004), 'Cutting Edge: TGF-α Induces a Regulatory Phenotype in CD4$^+$CD25$^-$ T Cells Through Foxp3 Induction and Down-Regulation of Smad7,' J Immunol, 172(9):5149-53.

Fantini MC et al., (2009) 'Smad7 Controls Resistance of Colitogenic T Cells to Regulatory T Cell-Mediated Suppression,' Gastroenterology, 136(4):1308-16.

International Search Report for PCT/EP2012/068146, mailed Mar. 6, 2013 (9 pages).

Maloy KJ and Powrie F, (2011) 'Intestinal Homeostasis and its Breakdown in Inflammatory Bowel Disease,' Nature, 474(7351):298-306.

Monteleone G et al., (2001), 'Blocking Smad7 Restores TGF-α1 Signaling in Chronic Inflammatory Bowel Disease,' J Clin Invest, 108(4):601-9.

Monteleone G et al., (2004) 'Smad7 in TGF-α-Mediated Negative Regulation of Gut Inflammation,' Trends Immunol, 25(10):513-7.

Monteleone G et al., (2011) 'Emerging Immunological Targets in Inflammatory Bowel Disease,' Curr Opin Pharmacol, 11(6):640-5.

Monteleone G et al., (2012) 'Phase I Clinical Trial of Smad7 Knockdown Using Antisense Oligonucleotide in Patients with Active Crohn's Disease,' Mol Ther, 20(4):870-6.

Navarro S. et al., (2011) 'The Oral Administration of Bacterial Extracts Prevents Asthma Via the Recruitment of Regulatory T Cells to the Airways,' Mucosal Immunol, 4(1):53-65.

Papadakis KA et al., (2003) 'CC Chemokine Receptor 9 Expression Defines a Subset of Peripheral Blood Lymphocytes with Mucosal T Cell Phenotype and Th1 or T-Regulatory 1 Cytokine Profile,' J Immunol, 171(1):159-65.

Papdakis KA et al., (2005) 'Dominant Role for TL1A/DR3 Pathway in IL-12 Plus IL-18-Induced IFN-α Production by Peripheral Blood and Mucosal CCR9+ T Lymphocytes,' J Immunol, 174(8):4985-90.

Strober W (2009) 'The Multifaceted Influence of the Mucosal Microflora on Mucosal Dendritic Cell Responses,' Immunity, 31(3):377-88.

Sutherland LR et al., (1987) '5-Aminosalicylic Acid Enema in the Treatment of Distal Ulcerative Colitis, Proctosigmoiditis, and Proctitis,' Gastroenterology, 92(6):1894-8.

Written Opinion of the International Searching Authority for PCT/EP2012/068146, mailed Mar. 6, 2013 (11 pages).

```
   1 ggcacgagcg gagagccgcg cagggcgcgg gccgcgcggg gtggggcagc cggagcgcag
  61 gccccgatc  ccccgcgggc gccccgggc  ccccgcgcgc gccccggcct ccgggagact
 121 ggcgcatgcc acgcagcgcc cctcgggccg ccgccgctcc tgcccggccc cctgctgctg
 181 ctgctgtcgc ctgccgcctgc tgccccaact ccgcgcccga cttcttcatg gtgtgcggag
 241 gtcatgttcg ctccttagca ggcaaacgac ttttctcctc gcctcctcgc cccgcatgtt
 301 caggaccaaa cgatctgcgc tcgtccggcg tctctggagg agccgtgcgc ccggcggcga
 361 ggacgaggag gagccgcag  ggggaggtgg acgaggaggc gagctgccgg gagaaggggc
 421 gacggacagc cgaccgcatg gggccggtgg ccgcggcccg ggcagggctg gatgctgcct
 481 gggcaaggcg gtgccaggtg ccaaaggtca ccaccatccc cacccgccag ccgcgggcgc
 541 cggcgcggcc ggggccgccg aggcggatct gaaggcgctc acgcactcgg tgctcaagaa
 601 actgaaggag cggcagctgg agctgctgct ccaggccgtg gagtcccgcc gcgggacgcg
 661 caccgcgtgc ctcctgctgc ccggccgcct gcactgcagg ctgggcccgg gggcgcccgc
 721 cggcgcgcag cctgcgcagc cgccctcgtc ctactcgctc ccctcctgc  tgtgcaaagt
 781 gttcaggtgg ccgcatctca ggcattcctc gcaagtcaag aggctgtctt gctgtgaatc
 841 ttacgggaag atcaaccccg agctggtgtg ctgcaacccc catcaccta  gccgactctg
 901 cgaactagag tctccccccc ctccttactc cagatacccg atggattttc tcaaaccaac
 961 tgcagactgt ccacatgctg tgccttcctc ccctgaaaca gggggaacga attatctggc
1021 ccctgggggg ctttcagatt cccaacttct tctggagcct ggggatccgt cacactggtg
1081 cgtggtggca tactcggagg agaagacgag actggggagg ctctactgtg tccaggagcc
1141 ctctctggat atcttctatg atctacctca gcggaatggc ttttgcctcg gacagctcaa
1201 ttcggacaac aagactcagc tggtgcagaa gctgcggagc aaaatcgcct gcggcatcca
1261 gctgacgcgg gagctggatg gtgtgtgggt gtacaaccgc agcagttacc ccatcttcat
1321 caagtccgcc acactggaca accggactc  caggacgtg  ttggtacaca aggtgttccc
1381 cggttLLcLcc aLcaaggcLL LcgacLacga gaaggcgLac agccLgcacc ggccccaaLga
1441 ccacgagttt atgcagcagc cgtggacggg ctttaccgtg cagatcacct ttgtgaaggg
1501 ctggggtcag tgctacaccc gccagttcat cagcagctgc ccgtgctcgc tagaggtcat
1561 cttcaacagc cggtagccgc gtgcggaggg gacagagcgt gagctgacca ggccacactt
1621 caaactactt tgctgctaat attttcctcc tcagtgcttg cttttcatgc aaactctttg
1681 gtcgttttttt ttttgtttgt tggttggttt tcttcttctc gtcctcgttt gtgttctgtt
1741 ttgtttcgct ctttcagaaa tagctatga  aaagaattgt tgggggtttt tttggaagaa
1801 ggggcaggta tgatcggcag gacaccctga taggaagagg ggaagcagaa atccaagcac
1861 caccaaacac agtctatgaa ggggggcggt catcatttca cttgtcacca gtgtgtgtga
1921 gtgtgagtgt gcggctgtgt gtgcacgcgt gtgcaggagc ggcagatggg gagacaacgt
1981 gctctttgtt ttgtgtctct tatggatgtc cccagcagag aggtttgcag tcccaagcgg
2041 tgtctctcct gccccttgga cacgctcagt gcgggcagag cagtacctgg gcaagctggc
2101 ggctggggtc ccagcagctg ccaggagcac gcctctgtcc ccagcctcgg aaagcccctg
2161 ccctcctct  cctcatcaa  ggacacgggc ctgtccacag gcttctgagc agcgagcctg
2221 ctagtggccg aaccagaacc aattattttc atccttgtct tattcccttc ctgccagccc
2281 ctgccattgt agcctctttc ttttttggcc atctgctcct ggatctccct gagatgggct
2341 tcccaagggc tgccgggca  gccccctcac actattgctc acccagtgcc ctctcccctc
2401 agcctctccc ctgcctgccc tggtgacatc acgttttcc  cggacttaca aaaccagctc
2461 agcactgcct gctcccatcc tgtgtgttaa gctctgctat taggccagca agcggggatg
2521 tccctgggag ggacatgctt agcagtcccc ttccctccaa gaaggatttg gtccgtcata
2581 acccaaggta ccatcctagg ctgacaccta actcttcttt catttcttct acaactcata
2641 cactcgtatg atacttcgac actgttctta gctcaatgag catgtttaca ctttaacata
2701 agctatttt  ctaactacaa aggtttaaat gaacaagaga agcattctca ttggaaattt
2761 agcattgtag tgctttgaga gagaaaggac tcctgaaaaa aaacctgaca tttattaaag
2821 aaaaaaatgt attttatgtt atatataaat atattattac ttgtaaatat aaagacgttt
2881 tataagcatc attatttatg tattgtgcaa tgtgtataaa caagaaaaat aaagaaaaga
2941 tgcactttgc tttaatataa atgcaaataa caaatgccaa attaaaaaag ataaacacaa
3001 gattggtgtt ttttcctatg ggtgttatca cctagctgaa tgttttttcta aaggagttta
3061 tgttccatta aaccattttt aaaatgtaca cttgaaaaaa aaaaaaaaa  a
(SEQ ID NO:1)
```

Fig. 1A

```
MFRTKRSALVRRLWRSRAPGGEDEEEGAGGGGGGGELRGEGATD
SRAHGAGGGGPGRAGCCLGKAVRGAKGHHHPHPPAAGAGAAGGAEADLKALTHSVLKK
LKERQLELLLQAVESRGGTRTACLLLPGRLDCRLGPGAPAGAQPAQPPSSYSLPLLLC
KVFRWPDLRHSSEVKRLCCCESYGKINPELVCCNPHHLSRLCELESPPPPYSRYPMDF
LKPTADCPDAVPSSAETGGTNYLAPGGLSDSQLLLEPGDRSHWCVVAYWEEKTRVGRL
YCVQEPSLDIFYDLPQGNGFCLGQLNSDNKSQLVQKVRSKIGCGIQLTREVDGVWVYN
RSSYPIFIKSATLDNPDSRTLLVHKVFPGFSIKAFDYEKAYSLQRPNDHEFMQQPWTG
FTVQISFVKGWGQCYTRQFISSCPCWLEVIFNSR
(SEQ ID NO:2)
```

Fig. 1B

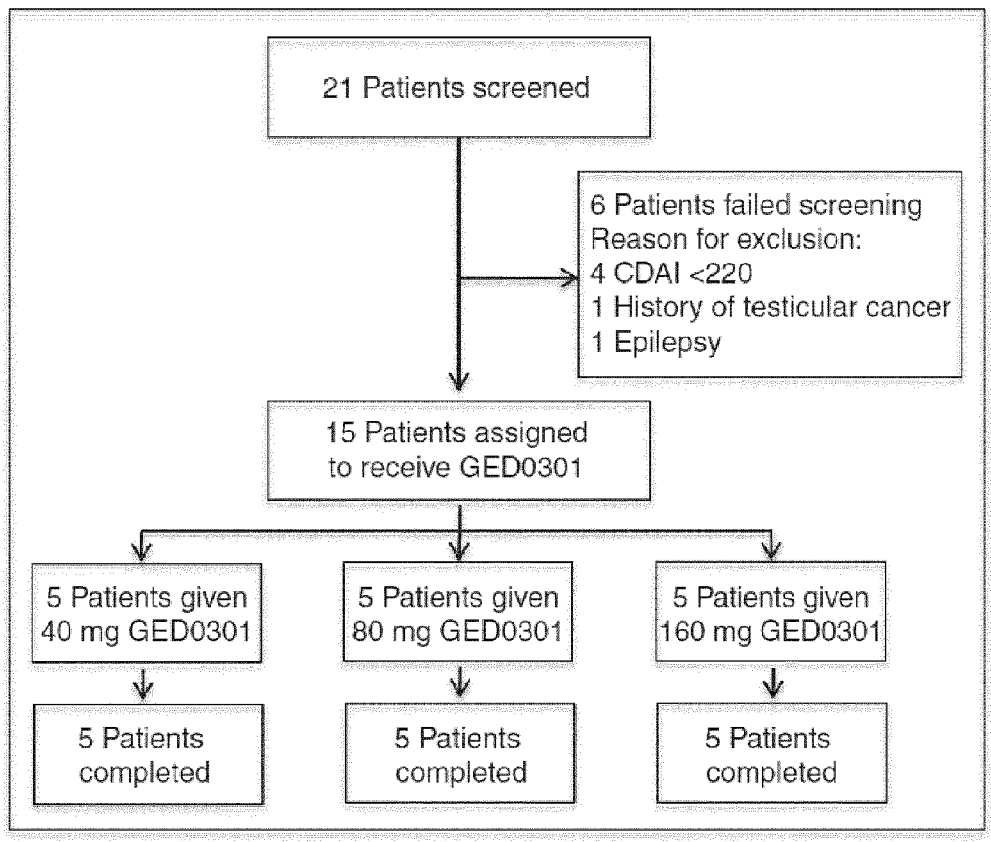

Fig. 2

|  | 40 mg | 80 mg | 160 mg | Overall |
|---|---|---|---|---|
|  | N = 5 | N = 5 | N = 5 | N = 15 |
|  | Cohort 1 | Cohort 2 | Cohort 3 |  |
| Gender, male: n (%) | 3 (60) | 4 (80) | 4 (80) | 11 (73) |
| Age: median (range) | 38 (32–41) | 34 (31–42) | 39 (24–45) | 37 (24–45) |
| Duration of CD: years median (range) | 6 (1–29) | 2 (1–5) | 1 (1–9) | 4 (1–29) |
| Previous I-C resection: n (%) | 4 (80) | 4 (80) | 1 (20) | 9 (60) |
| *CD location: n (%)* |  |  |  |  |
| Terminal ileum | 1 (20) | 1 (20) | 4 (80) | 6 (40) |
| Preanastomotic | 4 (80) | 4 (80) | 1 (20) | 9 (60) |
| CD behavior: n (%) inflammatory | 5 (100) | 5 (100) | 5 (100) | 15 (100) |
| *Concomitant medication: n (%)* |  |  |  |  |
| Sistemic corticosteroid | 0 (0) | 0 (0) | 1 (20) | 1 (6.6) |
| Budesonide | 4 (80) | 2 (40) | 3 (60) | 9 (60) |
| Mesalamine | 3 (60) | 4 (80) | 5 (100) | 12 (80) |
| *Intolerance or unresponsiveness: n (%)* |  |  |  |  |
| Immunosuppressive drugs | 1 (20) | 2 (40) | 2 (40) | 5 (33.3) |
| Anti-TNF | 1 (20) | 2 (40) | 2 (40) | 5 (33.3) |

*Abbreviations*: CD, Crohn's disease; TNF, tumor necrosis factor.

Fig. 3

| | Cohort 1 No. of events | Cohort 2 No. of events | Cohort 3 No. of events | Grade | Association with study drug |
|---|---|---|---|---|---|
| CD relapse | 0 | 1 | 0 | Mild | UN (1) |
| Abdominal pain | 0 | 0 | 2 | Severe | UN (2) |
| Vomiting | 0 | 0 | 2 | Severe | UN (2) |
| triglycerides and/or cholesterol increased | 0 | 0 | 3 | Mild | NT (3) |
| | 2 | 0 | 0 | Mild | UN (2) |
| | 1 | 0 | 0 | Mild | PR (1) |
| Bilirubin increased | 3 | 0 | 0 | Mild | NT (3) |
| Lymphocyte count increased | 0 | 0 | 1 | Mild | NT (1) |
| Serum potassium decreased | 1 | 0 | 0 | Mild | NT (1) |
| Urinary leukocyte count increased | 1 | 0 | 0 | Mild | NT (1) |
| | 0 | 0 | 1 | Mild | UN (1) |
| Urinary leukocyte esterases count increased | 1 | 0 | 0 | Mild | NT (1) |
| Urinary tract infection | 1 | 2 | 0 | Mild | NT (3) |
| Hypertension | 0 | 1 | 0 | Mild | NT (1) |
| ECG alteration (inversion of T waves) | 0 | 1 | 0 | Mild | UN (1) |
| Rhinitis | 1 | 0 | 0 | Mild | UN (1) |

Data indicate number of patients with at least one adverse event (number of patients with the documented association).
*Abbreviations:* CD, Crohn's disease; ECG, electrocardiogram; NT, not related to study drug; PR, probably related to study drug; UN, unlikely to be related to study drug.

Fig. 4

|  | Baseline | Day 8 | Day 28 |
|---|---|---|---|
| *Cells* | | | |
| $CD3^+$ | 66.8% ± 12.5% | 70.8% ± 12.5% | 70.4% ± 10.3% |
| $CD4^+$ | 44.8% ± 14.2% | 50.4% ± 12.8% | 50.7% ± 12.6% |
| $CD8^+$ | 16.6% ± 6.6% | 20.0% ± 6.2% | 19.8% ± 5.4% |
| $CD25^+$ | 44.2% ± 15.5% | 39.2% ± 11.6% | 39.4% ± 13.8% |
| $CD161^+$ | 4.9% ± 2.8% | 4.3% ± 2.7% | 4.7% ± 4.6% |
| $CD62L^+$ | 50.3% ± 13.7% | 54.9% ± 11.6% | 54.9% ± 12.9% |
| $CCR9^+$ | 2.9% ± 1.6% | 3.8% ± 3.1% | 3.6% ± 2.8% |
| $\alpha 4\beta 7^+$ | 3.0% ± 1.5% | 2.7% ± 2.1% | 2.4% ± 1.3% |

Fig. 7

|  | 40 mg | 80 mg | 160 mg | Overall |
|---|---|---|---|---|
|  | N = 5 | N = 5 | N = 5 | N = 15 |
|  | Cohort 1 | Cohort 2 | Cohort 3 |  |
| CDAI |  |  |  |  |
| Baseline | 289 (221–306) | 287 (252–400) | 287 (221–400) | 287 (221–400) |
| Day 8 | 86 (41–163) | 126 (70–215) | 53 (37–113) | 89 (37–215) |
| Day 28 | 93 (18–144) | 133 (52–301) | 71 (31–88) | 88 (18–301) |

*spec3106*

SEQUENCE LISTING

<160> NUMBER OF SEQ ID NOS: 9

<210> SEQ ID NO 1
<211> LENGTH: 3111
<212> TYPE: DNA
<213> ORGANISM: Homo sapiens

<400> SEQUENCE: 1

```
ggcacgagcg gagagccgcg cagggcgcgg gccgcgcggg gtggggcagc cggagcgcag      60
gcccccgatc cccggcgggc gcccccgggc ccccgcgcgc gccccggcct ccgggagact     120
ggcgcatgcc acggagcgcc cctcgggccg ccgccgctcc tgcccgggcc cctgctgctg     180
ctgctgtcgc ctgcgcctgc tgccccaact cggcgcccga cttcttcatg gtgtgcggag     240
gtcatgttcg ctccttagca ggcaaacgac ttttctcctc gcctcctcgc cccgcatgtt     300
caggaccaaa cgatctgcgc tcgtccggcg tctctggagg agccgtgcgc ccggcggcga     360
ggacgaggag gagggcgcag ggggaggtgg aggaggaggc gagctgcggg gagaaggggc     420
gacggacagc cgagcgcatg gggccggtgg cggcggcccg ggcagggctg gatgctgcct     480
gggcaaggcg gtgcgaggtg ccaaaggtca ccaccatccc cacccgccag ccgcgggcgc     540
cggcgcggcc ggggcgccg aggcggatct gaaggcgctc acgcactcgg tgctcaagaa     600
actgaaggag cggcagctgg agctgctgct ccaggccgtg gagtccgcg gcgggacgcg     660 caccgcgtgc ctcctgctgc ccggccgcct ggactgcagg ctgggcccgg gggcgcccgc     720
cggcgcgcag cctgcgcagc cgccctcgtc ctactcgctc cccctcctgc tgtgcaaagt     780
```

```
gttcaggtgg ccggatctca ggcattcctc ggaagtcaag aggctgtgtt gctgtgaatc      840
ttacgggaag atcaaccccg agctggtgtg ctgcaacccc catcaccttg gccgactctg      900
cgaactagag tctccccccc ctccttactc cagatacccg atggatttc tcaaaccaac      960 tgcagactgt ccagatgctg tgccttcctc cgctgaaaca gggggaacga attatctggc     1020
ccctgggggg ctttcagatt cccaacttct tctggagcct ggggatcggt cacactggtg     1080
cgtggtggca tactgggagg agaagacgag agtggggagg ctctactgtg tccaggagcc     1140
ctctctggat atcttctatg atctacctca ggggaatggc ttttgcctcg gacagctcaa     1200
ttcggacaac aagagtcagc tggtgcagaa ggtgcggagc aaaatcggct gcggcatcca     1260
gctgacgcgg gaggtggatg tgtgtgggt gtacaaccgc agcagttacc ccatcttcat      1320
caagtccgcc acactggaca acccggactc caggacgctg ttggtacaca aggtgttccc     1380
cggtttctcc atcaaggctt tcgactacga gaaggcgtac agcctgcagc ggcccaatga     1440
ccacgagttt atgcagcagc cgtggacggg ctttaccgtg cagatcagct ttgtgaaggg     1500
ctggggtcag tgctacaccc gccagttcat cagcagctgc ccgtgctggc tagaggtcat     1560
cttcaacagc cggtagccgc gtgcggaggg gacagagcgt gagctgagca ggccacactt     1620
caaactactt tgctgctaat attttcctcc tgagtgcttg cttttcatgc aaactctttg     1680
gtcgtttttt ttttgtttgt tggttggttt tcttcttctc gtcctcgttt gtgttctgtt     1740
ttgtttcgct ctttgagaaa tagcttatga aagaattgt tgggggtttt tttggaagaa      1800
ggggcaggta tgatcggcag acaccctga taggaagagg ggaagcagaa atccaagcac      1860
caccaaacac agtgtatgaa gggggcggt catcatttca cttgtcagga gtgtgtgtga      1920
gtgtgagtgt gcggctgtgt gtgcacgcgt gtgcaggagc ggcagatggg gagacaacgt     1980
gctctttgtt ttgtgtctct tatggatgtc cccagcagag aggtttgcag tcccaagcgg     2040
tgtctctcct gcccccttgga cacgctcagt ggggcagagg cagtacctgg gcaagctggc    2100 ggctgggtc ccagcagctg ccaggagcac ggctctgtcc ccagcctggg aaagcccctg      2160
cccctcctct ccctcatcaa ggacacgggc ctgtccacag gcttctgagc agcgagcctg     2220
ctagtggccg aaccagaacc aattattttc atccttgtct tattcccttc ctgccagccc    2280
ctgccattgt agcgtctttc ttttttggcc atctgctcct ggatctccct gagatgggct    2340
tcccaagggc tgccggggca gcccctcac agtattgctc acccagtgcc ctctccctc     2400 agcctctccc ctgcctgccc tggtgacatc aggttttcc cggacttaga aaaccagctc    2460
agcactgcct gctcccatcc tgtgtgttaa gctctgctat taggccagca agcggggatg    2520
tccctgggag ggacatgctt agcagtcccc ttccctccaa gaaggatttg gtccgtcata    2580
acccaaggta ccatcctagg ctgacaccta actcttcttt catttcttct acaactcata    2640
cactcgtatg atacttcgac actgttctta gctcaatgag catgtttaga ctttaacata    2700
agctattttt ctaactacaa aggtttaaat gaacaagaga agcattctca ttggaaattt    2760
agcattgtag tgctttgaga gagaaaggac tcctgaaaaa aaacctgaga tttattaaag    2820
aaaaaaatgt attttatgtt atatataaat atattattac ttgtaaatat aaagacgttt    2880
tataagcatc attatttatg tattgtgcaa tgtgtataaa caagaaaaat aaagaaaaga    2940
tgcactttgc tttaatataa atgcaaataa caaatgccaa attaaaaaag ataaacacaa    3000
gattggtgtt ttttcctatg ggtgttatca ccctagctga atgttttcta aaggagttta    3060
tgttccatta aacgattttt aaaatgtaca cttgaaaaaa aaaaaaaaa a              3111
```

```
<210> SEQ ID NO 2
<211> LENGTH: 427
<212> TYPE: PRT
<213> ORGANISM: Homo sapiens

<400> SEQUENCE: 2

Met Phe Arg Thr Lys Arg Ser Ala Leu Val Arg Arg Leu Trp Arg Ser
1               5                   10                  15

Arg Ala Pro Gly Gly Glu Asp Glu Glu Gly Ala Gly Gly Gly
            20                  25                  30

Cys Gly Gly Glu Leu Arg Gly Glu Gly Ala Thr Asp Ser Arg Ala His
            35                  40                  45

Gly Ala Gly Gly Gly Pro Gly Arg Ala Gly Cys Cys Leu Gly Lys
50                  55                  60

Ala Val Arg Gly Ala Lys Gly His His His Pro His Pro Pro Ala Ala
65                  70                  75                  80

Gly Ala Gly Ala Ala Gly Gly Ala Glu Ala Asp Leu Lys Ala Leu Thr
                85                  90                  95

His Ser Val Leu Lys Lys Leu Lys Glu Arg Gln Leu Glu Leu Leu Leu
            100                 105                 110

Gln Ala Val Glu Ser Arg Gly Gly Thr Arg Thr Ala Cys Leu Leu Leu
            115                 120                 125

Pro Gly Arg Leu Asp Cys Arg Leu Gly Pro Gly Ala Pro Ala Gly Ala
130                 135                 140

Gln Pro Ala Gln Pro Pro Ser Ser Tyr Ser Leu Pro Leu Leu Leu Cys
145                 150                 155                 160

Lys Val Phe Arg Trp Pro Asp Leu Arg His Ser Ser Glu Val Lys Arg
                165                 170                 175

Ile Leu Cys Cys Cys Glu Ser Tyr Gly Lys Ile Asn Pro Glu Leu Val
            180                 185                 190

Cys Cys Asn Pro His His Leu Ser Arg Leu Cys Glu Leu Glu Ser Pro
            195                 200                 205

Pro Pro Pro Tyr Ser Arg Tyr Pro Met Asp Phe Leu Lys Pro Thr Ala
210                 215                 220

Asp Cys Pro Asp Ala Val Pro Ser Ser Ala Glu Thr Gly Gly Ile Asn
225                 230                 235                 240

Tyr Leu Ala Pro Gly Gly Leu Ser Asp Ser Gln Leu Leu Glu Pro
                245                 250                 255

Gly Asp Arg Ser His Trp Cys Val Val Ala Tyr Trp Glu Glu Lys Thr
                260                 265                 270

Arg Val Gly Arg Leu Tyr Cys Val Gln Glu Pro Ser Leu Asp Ile Phe
            275                 280                 285

Tyr Asp Leu Pro Gln Gly Asn Gly Phe Cys Leu Gly Gln Leu Asn Ser
            290                 295                 300

Asp Asn Lys Ser Gln Leu Val Gln Lys Val Arg Ser Lys Ile Gly Cys
305                 310                 315                 320

Gly Ile Gln Leu Thr Arg Glu Val Asp Gly Val Trp Val Tyr Asn Arg
                325                 330                 335

Ser Ser Tyr Pro Ile Phe Ile Lys Ser Ala Thr Leu Asp Asn Pro Asp
            340                 345                 350

Ser Arg Thr Leu Leu Val His Lys Val Phe Pro Gly Phe Ser Ile Lys
            355                 360                 365

Ala Phe Asp Tyr Glu Lys Ala Tyr Ser Leu Gln Arg Pro Asn Asp His
            370                 375                 380
```

```
Glu Phe Met Gln Gln Pro Trp Thr Gly Phe Thr Val Gln Ile Ser Phe
385                 390                 395                 400

Val Lys Gly Trp Gly Gln Cys Tyr Thr Arg Gln Phe Ile Ser Ser Cys
            405                 410                 415

Pro Cys Trp Leu Glu Val Ile Phe Asn Ser Arg
            420                 425

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      anti-SMAD7 oligonucleotide

<400> SEQUENCE: 3
gtcgcccctt ctccccgcag c                                            21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      anti-SMAD7 oligonucleotide
<220> FEATURE:
<221> NAME/KEY: modified_base
<222> LOCATION: (3)..(3)
<223> OTHER INFORMATION: Cytosine, 5-methylcytosine or
      2'-O-methylcytosine
<220> FEATURE:
<221> NAME/KEY: modified_base
<222> LOCATION: (4)..(4)
<223> OTHER INFORMATION: Guanine, 5-methylguanine or
      2'-O-methylguanine
<220> FEATURE:
<221> NAME/KEY: modified_base
<222> LOCATION: (16)..(16)
<223> OTHER INFORMATION: Cytosine, 5-methylcytosine or
      2'-O-methylcytosine
<220> FEATURE:
<221> NAME/KEY: modified_base
<222> LOCATION: (17)..(17)
<223> OTHER INFORMATION: Guanine, 5-methylguanine or
      2'-O-methylguanine
<220> FEATURE:
<221> NAME/KEY: misc_feature
<222> LOCATION: (1)..(20)
<223> OTHER INFORMATION: At least one of the nucleotides 3, 4, 16 or 17
      is a methylated base

<400> SEQUENCE: 4
gtnncccctt ctcccnncag                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      anti-SMAD7 oligonucleotide
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
```

```
<400> SEQUENCE: 5
gtngcccctt ctcccngcag                                                20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      anti-SMAD7 oligonucleotide
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate

<400> SEQUENCE: 6
gtngcccctt ctcccngcag c                                              21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      anti-SMAD7 oligonucleotide
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 7
ntngcccctt ctcccngcan                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      anti-SMAD7 oligonucleotide
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate
<220> FEATURE:
<221> NAME/KEY: modified_base
<222> LOCATION: (20)..(20)
<223> OTHER INFORMATION: 2'-deoxyguanosine methylphosphonate
```

```
<400> SEQUENCE: 8
ntngcccctt ctcccngcan                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      anti-SMAD7 oligonucleotide
<220> FEATURE:
<221> NAME/KEY: modified_base
<222> LOCATION: (3)..(3)
<223> OTHER INFORMATION: 5-methyl 2'-deoxycytidine 5'-monophosphate
<220> FEATURE:
<221> NAME/KEY: modified_base
<222> LOCATION: (16)..(16)
<223> OTHER INFORMATION: 5-methyl 2'-deoxycytidine 5'-monophosphate

<400> SEQUENCE: 9
gtngcccctt ctcccngcag                                               20
```

METHODS OF MONITORING RESPONSIVENESS TO ANTI-SMAD7 THERAPY

REFERENCE TO RELATED APPLICATIONS

This application is the U.S. national stage of International (PCT) Patent Application No. PCT/EP2012/068146, filed Sep. 14, 2012, and published under PCT Article 21(2) in English which claims the benefit of and priority to European application EP 11425234.9, filed Sep. 15, 2011, and U.S. application 61/576,556, filed Dec. 16, 2011, the complete disclosures of which are hereby incorporated by reference into the present application for all purposes.

BACKGROUND

Inflammatory bowel disease (IBD) is a chronic inflammatory disorder of the gastrointestinal tract suffered by approximately one million patients in the United States. The two most common forms of IBD are Crohn's disease (CD) and ulcerative colitis (UC). Although CD can affect the entire gastrointestinal tract, it primarily affects the ileum (the distal or lower portion of the small intestine) and the large intestine. UC primarily affects the colon and the rectum. Current treatment for both CD and UC include aminosalicylates (e.g., 5-aminosalicylic acid, sulfasalazine and mesalamine), antibiotics (e.g., ciprofloxacin and metronidazole), corticosteroids (e.g., budesonide or prednisone), immunosuppressants (e.g., azathioprine or methotrexate) and tumor necrosis factor (TNF) antagonists (e.g., infliximab (Remicade®)). Patient response to these therapies varies with disease severity and it can vary over cycles of active inflammation and remission. Moreover, many of the current therapies for IBD are associated with undesirable side effects.

Although the etiologies of CD and UC are unknown, both are considered inflammatory diseases of the intestinal mucosa. Recent studies have demonstrated that TGF-β1 acts as a potent immunoregulator able to control mucosal intestinal inflammation. TGF-β1 binds a heterodimeric transmembrane serine/threonine kinase receptor containing two subunits, TGF-β1 R1 and TGF-β1 R2. Upon ligand binding, the TGF-β1 R1 receptor is phosphorylated by the constitutively active TGF-β1 R2 receptor and signal is propagated to the nucleus by proteins belonging to the SMAD family. Activated TGF-β1 R1 directly phosphorylates SMAD2 and SMAD3 proteins, which then interact with SMAD4. The complex of SMAD2/SMAD3/SMAD4 translocates to the nucleus and modulates the transcription of certain genes.

Additional studies have demonstrated that another SMAD protein, SMAD7, also plays a role in inflammation. SMAD7, an intracellular protein, has been shown to interfere with binding of SMAD2/SMAD3 to the TGF-β1 R1 preventing phosphorylation and activation of these proteins. Further, increased expression of SMAD7 protein is associated with an inhibition of TGF-β1 mediated-signaling. Mucosal samples from IBD patients are characterized by high levels of SMAD7 and reduced levels of phosphorylated-SMAD3 indicating that TGF-β1-mediated signaling is compromised in these patients.

Recent studies have focused on SMAD7 as a target for treating patients suffering from IBD. Such therapies include anti-SMAD7 antisense therapies. As such, there is a need for methods based on predictive biomarkers that can be used to identify patients that are likely (or unlikely) to respond to treatment with anti-SMAD7 therapies.

SUMMARY

The invention is based, in part, on the discovery that modulation of certain T cell populations (e.g., increased CCR9+FoxP3+ T cells, reduced CCR9+ IFN-gamma positive (IFN-γ+) T cells, reduced CCR9+ IL17A+ T cells, reduced FoxP3+ T cells, reduced IFN-γ+ T cells and/or reduced IL17A+ T cells) in a biological (for example, blood or tissue) sample from a subject (e.g., a human patient) suffering from Inflammatory Bowel Disease (IBD) (e.g., Crohn's Disease or Ulcerative Colitis) correlate with sensitivity to treatment with an anti-SMAD7 therapy.

It will be appreciated that it is advantageous to be able to predict in advance or shortly after commencing treatment, whether an IBD patient is likely to be responsive to treatment with an anti-SMAD7 therapy. Modulation of the cell populations as described herein are predictive of the efficacy of the treatment of a subject having IBD with an anti-SMAD7 therapy. Advantageously, the methods of the invention will ultimately assist physicians in choosing effective therapies and lead to improvements in a patient's disease status, better medical care and reduction in over all patient costs.

Accordingly, in a first aspect, the invention provides a method for determining the responsiveness of a subject having Inflammatory Bowel Disease (IBD) to treatment with at least one anti-SMAD7 therapy, the method comprising:
  determining the amount of at least one cell population selected from the group consisting of: CCR9+ FoxP3+ T cells, CCR9+ IFN-gamma+ T cells, CCR9+ IL17A+ T cells, FoxP3+ T cells, IFN-gamma+ T cells and IL17A+ T cells, in at least one sample obtained from the subject,
  wherein, increased amounts of the cell population CCR9+ FoxP3+ T cells, and/or decreased amounts of at least one of the cell populations CCR9+ IFN-gamma+ T cells, CCR9+ IL17A+ T cells, FoxP3+ T cells, IFN-gamma+ T cells and IL17A+ T cells, in the at least one sample relative to a known control level of the at least one cell population is predictive of responsiveness of the subject having IBD to the anti-SMAD7 therapy.

It is to be appreciated that "determining the responsiveness of a subject" includes predicting or monitoring the effectiveness or responsiveness of a subject having IBD to treatment with at least one anti-SMAD7 therapy.

Suitably, the sample is a biological sample.

In a preferred embodiment of the method of the invention, identification of modulation of two or more of the following may assist in determining the responsiveness of the subject to the therapy:
  an increase in the amount of CCR9+ FoxP3+ T cells indicates that the subject is likely to respond, or is responsive, to the anti-SMAD7 therapy;
  a decrease in the amount of CCR9+ IFN-gamma+ T cells indicates that the subject is likely to respond, or is responsive, to the anti-SMAD7 therapy;
  decrease in the amount of CCR9+ IL17A+ T cells indicates that the subject is likely to respond, or is responsive, to the anti-SMAD7 therapy;
  a decrease in the amount of FoxP3+ T cells indicates that the subject is likely to respond, or is responsive, to the anti-SMAD7 therapy;
  a decrease in the amount of IFN-gamma+ T cells indicates that the subject is likely to respond, or is responsive, to the anti-SMAD7 therapy; and a decrease in the amount of IL17A+ T cells indicates that the subject is likely to respond, or is responsive, to the anti-SMAD7 therapy.

In a first preferred embodiment, the cell population are CCR9+ FoxP3+ T cells. In a second preferred embodiment, the cell population are CCR9+ IFN-gamma+ T cells. In a third preferred embodiment, the cell population are CCR9+ IL17A+ T cells. In a fourth preferred embodiment, the preferred cell population are FoxP3+ T cells. In a fifth preferred embodiment, the cell population are IFN-gamma+ T cells. In a sixth preferred embodiment, the cell population are IL17A+ T cells. Other preferred cell populations are any of FoxP3+CD103+ T cells, CD103+ T cells or integrin α4β7+ T cells.

Suitably, the methods of the invention may be carried out in vitro.

Preferably, in the methods of the invention, the amount determining step may be preceded by a step of obtaining the sample from a subject suffering from IBD. The sample may be taken by withdrawing blood or performing tissue biopsy.

Suitably, the subject may be receiving at least one anti-SMAD7 therapy when the at least one sample is obtained from the subject.

Preferably, in the method of the invention, identification of an increase in the amount of CCR9+ FoxP3+ T cells, a decrease in the amount of CCR9+ IFN-gamma+ T cells, a decrease in the amount of CCR9+ IL17A+ T cells, a decrease in the amount of FoxP3+ T cells, a decrease in the amount of IFN-γ+ T cells or a decrease in the amount of IL17A+ T cells indicates that the subject is likely to enter remission.

Suitably, the amount of the at least one cell population may be determined by flow cytometry, by immunohistochemistry (for example, ELISA) and/or by RNA/DNA analysis using reagents/method known to those skilled in the art.

It will be appreciated that the flow cytometry and/or the immunohistochemistry may be performed using an antibody selected from the group consisting of: an anti-CCR9 antibody, an anti-FoxP3 antibody, an anti-IFN-gamma antibody and an anti-IL17A antibody.

Alternatively, determining the amount of cells may be performed by measuring the amount of RNA encoding at least one marker selected from the group consisting of: CCR9, FoxP3, IFN-gamma, and IL17A.

Preferably, the control means a control level, which is a baseline level of amounts of the at least one cell population obtained from the patient's (having IBD) sample prior to administration of at least one anti-SMAD7 therapy or obtained immediately after the administration of at least one anti-SMAD7 therapy. By immediately after administration it is meant on the first/same day the treatment is commenced.

In a related aspect, disclosed herein is a method for monitoring a subject suffering from IBD who is undergoing treatment with an anti-SMAD7 therapy to determine if the subject is responsive to the therapy, and/or to determine if therapy should be continued. The method includes: (a) determining the amounts of at least one of CCR9+ FoxP3+ T cells, CCR9+ IFN-γ+ T cells, CCR9+ IL17A+ T cells, FoxP3+ T cells, IFN-γ+ T cells and IL17A+ T cells in a sample obtained from a subject having IBD and who is receiving an anti-SMAD7 therapy; and (b) comparing the amounts in the sample with a control level of at least one of CCR9+ FoxP3+ T cells, CCR9+ IFN-γ+ T cells, CCR9+ IL17A+ T cells, FoxP3+ T cells, IFN-γ+ T cells and IL17A+ T cells, respectively. A subject may be identified as responsive (e.g., sensitive) to therapy and/or likely to continue to respond to treatment with an anti-SMAD7 therapy if there is an increase in the amount of CCR9+ FoxP3+ T cells in the sample obtained from the subject compared to the control, or if there is a decrease in the amounts of at least one of CCR9+ IFN-γ+ T cells, CCR9+ IL17A+ T cells, FoxP3+ T cells, IFN-γ+ T cells and IL17A+ T cells in a sample obtained from the subject compared to the control. Alternatively, a subject may be identified as non-responsive (e.g., resistant) to treatment and/or unlikely to continue to respond to treatment with an anti-SMAD7 therapy if there is a decrease in the amount of CCR9+ FoxP3+ T cells in the sample obtained from the subject compared to the control, or if there is an increase in the amounts of at least one of CCR9+ IFN-γ+ T cells, CCR9+ IL17A+ T cells, FoxP3+ T cells, IFN-γ+ T cells and IL17A+ T cells in a sample obtained from the subject compared to the control.

In another aspect, disclosed herein is a method of identifying subjects suffering from IBD who are likely to be responsive, or are responsive, to treatment with an anti-SMAD7 therapy (e.g., an anti-SMAD7 antisense oligonucleotide). The method includes: (a) determining the amounts of at least one of CR9+ FoxP3+ T cells, CCR9+ IFN-γ+ T cells, CCR9+ IL17A+ T cells, FoxP3+ T cells, IFN-γ+ T cells and IL17A+ T cells in a sample obtained from a subject suffering from IBD; and (b) comparing the amounts in the sample with a control level of at least one of CCR9+ FoxP3+ T cells, CCR9+ IFN-gamma+ T cells, CCR9+ IL17A+ T cells, FoxP3+ T cells, IFN-γ+ T cells and IL17A+ T cells, respectively. A subject may be identified as likely to respond, or responsive (e.g., sensitive), to treatment with an anti-SMAD7 therapy if there is an increase in the amount of CCR9+ FoxP3+ T cells in the sample obtained from the subject compared to the control, or if there is a decrease in the amounts of at least one of CCR9+ IFN-γ+ T cells, CCR9+ IL17A+ T cells, FoxP3+ T cells, IFN-γ+ T cells and IL17A+ T cells in a sample obtained from the subject compared to the control. Alternatively, a subject may be identified as unlikely to respond, or non-responsive (e.g., resistant), to treatment with an anti-SMAD7 therapy if there is a decrease in the amount of CCR9+ FoxP3+ T cells in the sample obtained from the subject compared to the control, or if there is a increase in the amounts of at least one of CCR9+ IFN-γ+ T cells, CCR9+ IL17A+ T cells, FoxP3+ T cells, IFN-γ+ T cells and IL17A+ T cells in a sample obtained from the subject compared to the control.

In other words, there is provided a method for determining the responsiveness of a subject suffering from Inflammatory Bowel Disease (IBD) to at least one anti-SMAD7 therapy, the method comprising:

(a) determining an amount of CCR9+ FoxP3+ T cells in a sample obtained from a subject suffering from IBD;

(b) comparing the amount of CCR9+ FoxP3+ T cells in the sample with a control level of CCR9+ FoxP3+ cells, wherein an increase in the amount of CCR9+ FoxP3+ T cells indicates that the subject is likely to respond, or is responsive, to the anti-SMAD7 therapy; and/or (a) determining an amount of CCR9+ IFN-gamma+ T cells in a sample obtained from a subject suffering from IBD;

(b) comparing the amount of CCR9+ IFN-gamma+ T cells in the sample with a control level of CCR9+ IFN-gamma+ cells, wherein a decrease in the amount of CCR9+ IFN-gamma+ T cells indicates that the subject is likely to respond, or is responsive, to the anti-SMAD7 therapy; and/or (a) determining an amount of CCR9+ IL17A+ T cells in a sample obtained from a subject suffering from IBD;

(b) comparing the amount of CCR9+ IL17A+ T cells in the sample with a control level of CCR9+ IL17A+ cells, wherein a decrease in the amount of CCR9+ IL17A+ T cells indicates that the subject is likely to respond, or is responsive, to the anti-SMAD7 therapy; and/or (a) determining an amount of FoxP3+ T cells in a sample obtained from a subject suffering from IBD;
(b) comparing the amount of FoxP3+ T cells in the sample with a control level of FoxP3+ T cells, wherein a decrease in the amount of FoxP3+ T cells indicates that the subject is likely to respond, or is responsive, to the anti-SMAD7 therapy; and/or (a) determining an amount of IFN-gamma+ T cells in a sample obtained from a subject suffering from IBD;
(b) comparing the amount of IFN-gamma+ T cells in the sample with a control level of IFN-gamma+ cells, wherein a decrease in the amount of IFN-gamma+ T cells indicates that the subject is likely to respond, or is responsive, to the anti-SMAD7 therapy; and/or (a) determining an amount of IL17A+ T cells in a sample obtained from a subject suffering from IBD;
(b) comparing the amount of IL17A+ T cells in the sample with a control level of IL17A+ cells, wherein a decrease in the amount of IL17A+ T cells indicates that the subject is likely to respond, or is responsive, to the anti-SMAD7 therapy.

In a related aspect there is provided at least one antibody against cell markers for at least one of CCR9+ FoxP3+ T cells, CCR9+ IFN-gamma+ T cells, CCR9+ IL17A+ T cells, FoxP3+ T cells, IFN-gamma+ T cells and IL17A+T, and FoxP3+CD103+ T cells, CD103+ T cells and integrin α4β7+ T cells, for use in a diagnostic method practiced on a human or animal body.

Suitably, the diagnostic method may be used to predict or monitor the responsiveness of a subject having Inflammatory Bowel Disease (IBD) to treatment with at least one anti-SMAD7 therapy or to determine the suitability of a subject having Inflammatory Bowel Disease (IBD) for treatment with at least one anti-SMAD7 therapy, to determine that the subject is likely to respond, or is responsive, to the anti-SMAD7 therapy and/or to determine whether the subject is likely to enter remission.

In a related embodiment, there is provided a kit comprising at least one of anti-CCR9 antibody, anti-FoxP3 antibody, anti-IFN-gamma antibody and/or anti-IL17A antibody for identifying cell populations or reagents for detecting expression of RNA encoding protein cell markers for at least one of CCR9+ FoxP3+ T cells, CCR9+ IFN-gamma+ T cells, CCR9+ IL17A+ T cells, FoxP3+ T cells, IFN-gamma+ T cells and IL17A+ T cells.

Suitably, the kit further comprises at least one of buffers, reagents and detailed instructions for identifying, sorting, and counting cells, using FACS technology.

Desirably, in the kit of the invention, the antibody is primary antibody against a CCR9 protein, a primary antibody against a FoxP3 protein, and a secondary antibody conjugated to a reporter enzyme, and the kit optionally further comprising at least buffers, reagents and detailed instructions for identifying cell populations using IHC technology.

Suitably, in the kit of the invention, there is included a capture antibody against a CCR9 protein, a detection antibody against a FoxP3 protein, and/or a secondary antibody conjugated to a reporter enzyme; and optionally further comprises buffers, reagents and detailed instructions for identifying cell populations using the ELISA technology.

It is contemplated herein that the disclosed methods, uses and kits can be used to personalize treatment of anti-SMAD7 therapies to subjects who are likely to be responsive or are responsive to such therapies.

It is also contemplated herein that the disclosed methods, uses and kits may be used to determine whether a subject is likely to enter remission after from suffering from IBD. For example, a subject may be identified as likely to enter remission if there is an increase in the amount of CCR9+ FoxP3+ T cells in the sample obtained from the subject compared to the control, and/or if there is a decrease in the amounts of CCR9+ IFN-γ+ T cells, CCR9+ IL17A+ T cells, CCR9+ IL17A+ T cells, FoxP3+ T cells, IFN-γ+ T cells and/or IL17A+ T cells in a sample obtained from the subject compared to the control.

As mentioned above, the sample obtained from the subject may be a blood sample, such as an isolated peripheral blood mononuclear cell sample. Alternatively, the sample obtained from the subject may be a tissue sample. For example, a tissue sample may be derived from the gastrointestinal tract of the subject (e.g., from the small intestine of the subject).

The control or control level sample may include a sample (e.g., a blood or tissue sample) obtained from the subject prior to treatment with an anti-SMAD7 therapy. The control sample provides a baseline level of the amounts of at least one cell populations of the invention present before treatment and which may be used for monitoring the subject's response to treatment. A control or control level sample may be obtained from the subject on the same day the anti-SMAD7 therapy is first administered (e.g., Day 1 of a treatment regimen). In other embodiments, a control or control level sample may be obtained from a subject at least one day prior to the start of an anti-SMAD7 therapy (e.g., Day 0 of a treatment regimen).

In certain embodiments, the amounts of at least one of CCR9+ FoxP3+ T cells, CCR9+ IFN-γ+ T cells, CCR9+ IL17A+ T cells, FoxP3+ T cells, IFN-γ+ T cells and IL17A+ T cells in a sample are determined by flow cytometry. In other embodiments, the determination is performed by immunohistochemistry or by an ELISA assay. FACS, immunohistochemistry, and ELISA assays may be performed using antibodies selected from the group consisting of at least one of an anti-CCR9 antibody, an anti-FoxP3 antibody, an anti-IFN-gamma antibody, and an anti-IL17A antibody. In another embodiment, the amount of a cell population is determined by measuring the amount of RNA encoding at least one marker selected from the group consisting of CCR9, FoxP3, IFN-gamma, and IL17A. In certain embodiments, the anti-SMAD7 therapy is an anti-SMAD7 antisense oligonucleotide. The anti-SMAD7 antisense oligonucleotide therapy may be an anti-SMAD7 antisense oligonucleotide selected from the group consisting of SEQ ID NO: 4, SEQ ID NO: 5, SEQ ID NO: 6, SEQ ID NO: 7, SEQ ID NO: 8 and SEQ ID NO: 9. In an exemplary embodiment, the SMAD7 antisense oligonucleotide comprises SEQ ID NO: 6.

The foregoing aspects and embodiments of the invention may be more fully understood by reference to the following figures, detailed description and claims.

BRIEF DESCRIPTION OF THE DRAWINGS

FIG. 1 (A) provides the nucleic acid sequence of SMAD7 (SEQ ID NO: 1) and (B) provides the amino acid sequence of SMAD7 (SEQ ID NO: 2).

FIG. 2 is a flow chart that shows the screening results of applicants and division of enrolled patients into cohorts.

FIG. 3 displays demographic and clinical characteristics related to the patients enrolled in the trial.

FIG. 4 illustrates different types of adverse events, their frequency during the trial, and their association with GED0301.

FIG. 7 displays the fraction of T cells that test positive for various markers at baseline and days 8 and 28 of the clinical trial.

DETAILED DESCRIPTION

Figure 5:
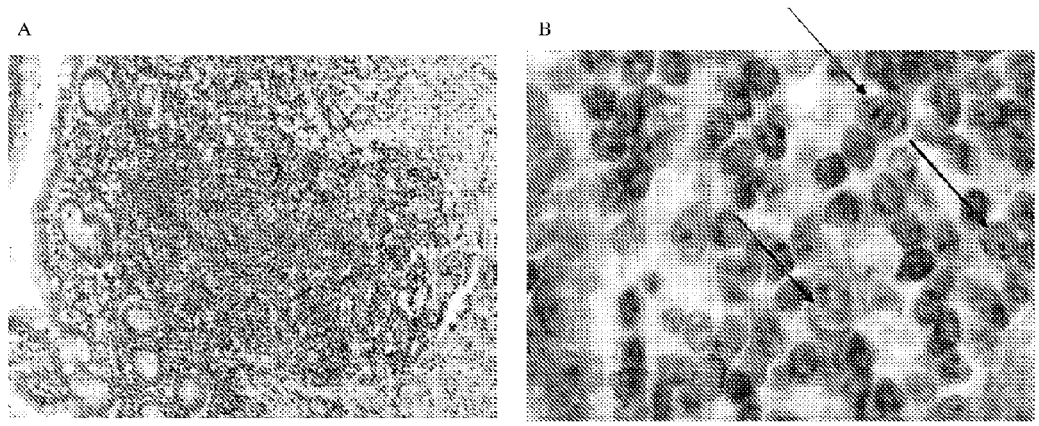
FIGS. 5 (A and B) are photographs of an immunohistochemical analysis showing that SMAD7 is expressed in human intestinal follicles and Peyer's Patches in a subject suffering from Crohn's disease. In B, the arrows show SMAD7 expression in the nucleus and cytoplasm. Panel A, 100× magnification; Panel B, 200× magnification.

Methods for monitoring whether a subject will be responsive (e.g., sensitive or resistant) to treatment with an anti-SMAD7 therapy are disclosed. The methods are based, in part, on the discovery that modulation of certain T cell populations (e.g., increased CCR9+ FoxP3+ T cells, reduced CCR9+ IFN-gamma positive (IFN-γ+) T cells, reduced CCR9+ IL17A+ T cells, reduced FoxP3+ T cells, reduced IFN-γ+ T cells and/or reduced IL17A+ T cells) in a blood sample from a subject suffering from IBD, e.g., Crohn's disease or ulcerative colitis, correlate with sensitivity to treatment with an anti-SMAD7 therapy.

As described herein, one or more T cell populations of a subject suffering from IBD and who is or has received treatment with an anti-SMAD7 therapy are monitored to determine if the subject is responsive to the therapy and/or to determine if therapy should be continued. In one aspect, the method comprises (a) determining the amounts of CCR9+ FoxP3+ T cells, CCR9+ IFN-γ+ T cells, CCR9+ IL17A+ T cells, FoxP3+ T cells, IFN-γ+ T cells and/or IL17A+ T cells in a sample obtained from a subject having IBD and who is receiving an anti-SMAD7 therapy; and (b) comparing the amounts in the sample with a control level of CCR9+ FoxP3+ T cells, CCR9+ IFN-γ+ T cells, CCR9+ IL17A+ T cells, FoxP3+ T cells, IFN-γ+ T cells and/or IL17A+ T cells, respectively. A subject may be identified as responsive (e.g., sensitive) to therapy and/or likely to continue to respond to treatment with an anti-SMAD7 therapy if there is an increase in the amount of CCR9+ FoxP3+ T cells in the sample obtained from the subject compared to the control and/or if there is a decrease in the amounts of CCR9+ IFN-γ+ T cells, CCR9+ IL17A+ T cells, FoxP3+ T cells, IFN-γ+ T cells and/or IL17A+ T cells in a sample obtained from the subject compared to the control.

Alternatively, a subject may be identified as non-responsive (e.g., resistant) to treatment and/or unlikely to continue to respond to treatment with an anti-SMAD7 therapy if there is a decrease in the amount of CCR9+ FoxP3+ T cells in the sample obtained from the subject compared to the control, or if there is an increase in the amounts of CCR9+ IFN-γ+ T cells, CCR9+ IL17A+ T cells, FoxP3+ T cells, IFN-γ+ T cells and/or IL17A+ T cells in a sample obtained from the subject compared to the control.

In another aspect, one or more T cell populations of a subject suffering from IBD are monitored to identify if the subject is likely to respond to treatment with an anti-SMAD7 therapy. The method includes: (a) determining the amounts of CCR9+ FoxP3+ T cells, CCR9+ IFN-γ+ T cells, CCR9+ IL17A+ T cells, FoxP3+ T cells, IFN-γ+ T cells and/or IL17A+ T cells in a sample obtained from a subject suffering from IBD; and (b) comparing the amounts in the sample with a control level of CCR9+ FoxP3+ T cells, CCR9+ IFN-gamma+ T cells, CCR9+ IL17A+ T cells, FoxP3+ T cells, IFN-γ+ T cells and/or IL17A+ T cells, respectively. A subject may be identified as likely to respond, or responsive (e.g., sensitive), to treatment with an anti-SMAD7 therapy if there is an increase in the amount of CCR9+ FoxP3+ T cells in the sample obtained from the subject compared to the control, and/or if there is a decrease in the amounts of CCR9+ IFN-γ+ T cells, CCR9+ IL17A+ T cells, CCR9+ IL17A+ T cells, FoxP3+ T cells, IFN-γ+ T cells and/or IL17A+ T cells in a sample obtained from the subject compared to the control.

Alternatively, a subject may be identified as unlikely to respond, or non-responsive (e.g., resistant), to treatment with an anti-SMAD7 therapy if there is a decrease in the amount of CCR9+ FoxP3+ T cells in the sample obtained from the subject compared to the control, and/or if there is a increase in the amounts of CCR9+ IFN-γ+ T cells, CCR9+ IL17A+ T cells, FoxP3+ T cells, IFN-γ+ T cells and/or IL17A+ T cells in a sample obtained from the subject compared to the control.

In certain embodiments, the amount of FoxP3+CD103+ T cells, CD103+ T cells and/or integrin α4β7+ T cells may also be measured. Subjects who are responsive to therapy display consistent amount of these cell populations during therapy compared to pre-treatment levels.

In other embodiments, the disclosed methods may be used to determine whether a subject is likely to enter remission after from suffering from IBD. For example, a subject may be identified as likely to enter remission if there is an increase in the amount of CCR9+ FoxP3+ T cells in the sample obtained from the subject compared to the control, and/or if there is a decrease in the amounts of CCR9+ IFN-γ+ T cells, CCR9+ IL17A+ T cells, CCR9+ IL17A+ T cells, FoxP3+ T cells, IFN-γ+ T cells and/or IL17A+ T cells in a sample obtained from the subject compared to the control.

For convenience, certain terms in the specification, examples, and appended claims are collected in this section.

As used herein, "CCR9" (chemokine (C-C motif) receptor 9 also known as CDw199, GPR-9-6, GPR28, C-C CKR-9, G protein-coupled receptor 28) means the human protein encoded by the gene identified by Entrez GeneID No. 10803 and allelic variants thereof.

As used herein, "FoxP3" (forkhead box P3 also known as JM2, AIID, DIETER, IPEX, MGC141961, MGC141963, PIDX, XPID) means the human protein encoded by the gene identified by Entrez GeneID No. 50943 and allelic variants thereof.

As used herein, "IFN-gamma" or "IFN-γ" (interferon gamma also known as IFNG, IFG, IFI) means the human protein encoded by the gene identified by Entrez GeneID No. 3458 and allelic variants thereof.

As used herein, "IL17A" (interleukin 17A also known as CTLA8, IL-17, IL-17A, IL17, cytotoxic T-lymphocyte-associated antigen 8; cytotoxic T-lymphocyte-associated protein 8; cytotoxic T-lymphocyte-associated serine esterase 8) means the human protein encoded by the gene identified by Entrez GeneID No. 3605 and allelic variants thereof.

As used herein, "CD103" (CD103 antigen also known as integrin, alpha e; mucosal lymphocyte antigen 1, alpha peptide; HUMINAE, integrin alpha-IEL; integrin alpha-E; HML-1 antigen; and MGC141996) means the human protein encoded by the gene identified by Entrez GeneID No. 3682 and allelic variants thereof.

As used herein, "α4β7" (integrin, alpha 4 beta 7 also known as gut homing receptor beta subunit and ITGB7) means the human gene encoded by the gene identified by Entrez GeneID No. 3695 and allelic variants thereof.

As used herein, "SMAD7" (also known as CRCS3, FLJ16482, MADH7, MADH8, MAD (mothers against decapentaplegic, *Drosophila*) homolog 7, MAD homolog 8, SMAD, mothers against DPP homolog 7, mothers against DPP homolog 8) means the human protein encoded by the gene identified by Entrez GeneID No. 4092 and allelic variants thereof.

As used herein, "Crohn's Disease Activity Index" or "CDAI" refers to a measurement or index used to assess the progress of patients suffering from CD as described by Best et al., GASTROENTEROLOGY, 70:439-44 (1976). CDAI scores of 150 or below are generally associated with inactive disease and are indicative of better prognosis than higher scores. Values above 150 are generally associated with active disease and values above 450 are associated with extremely severe disease. CDAI scores may be used to determine how well a patient is responding to therapy and may be used to identify patients in remission. In certain embodiments, a benchmark clinical response means that the subject displays a decrease in CDAI score by at least 100 points. In a clinical trial, a CDAI score of 150 or below is generally associated with remission.

As used herein, "Ulcerative Colitis Disease Activity Index" or "UCDAI" refers to a measurement or index used to assess the progress of patients suffering from UC as described by Sutherland et al., Gastroenterology, 92:1894-98 (1987). The UCDAI is a series of qualifiers about the symptoms of UC including stool frequency, rectal bleeding, the appearance of the colon lining, and a physician's rating of disease activity. Each of these qualifiers is given a number from 0 to 3, with 3 being the highest disease activity. In a clinical trial, remission is often defined as a UCDAI score of 1 or less, and improvement is a reduction of 3 or more points from the score at the beginning of the trial. UCDAI may be used in clinical trials to determine how well a patient is responding to therapy and may be used to identify patients in remission. Other commonly used indices for measuring disease severity in UC patients include the Truelove and Witts Index, the St. Mark's Index, the Simple Clinical Colitis Activity Index (SCCAI), the Lichtiger Index, the Ulcerative Colitis Symptom Score (UCSS), and the Mayo Clinic Score.

As used herein, "response" or "responding" to treatment means that a subject with Crohn's disease displays: (a) a decrease in CDAI score, e.g., a decrease in CDAI score by 20 points, 30 points, 40 points, 50 points, 60 points, 70 points, 80 points, 90 points, 100 points or more; (b) a CDAI score of less than 150; and/or (c) the induction of remission. With respect to a subject with UC, "response" or "responding" to treatment means that the subject displays (a) a decrease in UCDAI score, e.g., a decrease in UCDAI score by 1 point, 2 points or more; (b) a UCDAI score of 1 or less; and/or (c) the induction of remission.

Anti-SMAD7 Therapy

Anti-SMAD7 therapy includes targeted therapies against SMAD7 (e.g., anti-SMAD7 antisense therapies and antibodies against SMAD7). Antisense oligonucleotides are short synthetic oligonucleotide sequences complementary to the messenger RNA (mRNA), which encodes for the target protein (e.g., SMAD7). Antisense oligonucleotide sequences hybridize to the mRNA producing a double-strand hybrid that can lead to the activation of ubiquitary catalytic enzymes, such as RNase H, which degrades DNA/RNA hybrid strands thus preventing protein translation.

In certain embodiments, an anti-SMAD7 antisense oligonucleotide may target site 403, 233, 294, 295, 296, 298, 299, and/or 533 (i.e., nucleotides 403, 233, 294, 295, 296, 298, 299, and 533, respectively) of the human SMAD7 mRNA (e.g., of SEQ ID NO: 1).

In certain embodiments, an antisense oligonucleotide may be derived from the following anti-SMAD7 antisense oligonucleotide 5'-GTCGCCCCTTCTCCCCGCAGC-3' (SEQ ID NO: 3).

It is contemplated herein that an antisense oligonucleotide targeting SMAD7 may comprise a mixed-backbone wherein the cytosine residues in a CpG pair are replaced by 5'-methylcytosine (abbreviated as Me-dC). Methylphosphonate linkages may also be placed at the 5' and/or 3' ends of an antisense oligonucleotide (abbreviated as MeP).

Exemplary antisense oligonucleotide therapies that target SMAD7 include, but are not limited to 5'-GTXYCCCCT-TCTCCCXYCAG-3' (SEQ ID NO: 4), wherein X is a nucleotide comprising a nitrogenous base selected from the group consisting of cytosine and 5-methylcytosine or a 2'-O-methylcytosine nucleoside, and wherein Y is a nucleotide comprising a nitrogenous base selected from the group consisting of guanine and 5-methylguanine or a 2'-O-methylguanine nucleoside, provided that at least one of the nucleotides X or Y comprises a methylated nitrogenous base;

5'-GTXGCCCCTTCTCCCXGCAG-3' (SEQ ID NO: 5), wherein X is 5-methyl 2'-deoxycytidine 5'-monophosphate;

5'-GTXGCCCCTTCTCCCXGCAGC-3' (SEQ ID NO: 6), wherein X is 5-methyl 2'-deoxycytidine 5'-monophosphate;

5'-ZTXGCCCCTTCTCCCXGCAZ-3' (SEQ ID NO: 7), wherein X is 5-methyl 2'-deoxycytidine 5'-monophosphate and Z is 2'-deoxyguanosine methylphosphonate;

5'-ZTXGCCCCTTCTCCCXGCAZ-3' (SEQ ID NO: 8), wherein X is 5-methyl 2'-deoxycytidine 5'-monophosphate and Z is 2'-deoxyguanosine methylphosphonate;

5'-GTXGCCCCTTCTCCCXGCAG-3' (SEQ ID NO: 9), wherein X is 5-methyl 2'-deoxycytidine 5'-monophosphate. (See, e.g., U.S. Pat. Nos. 7,807,818 and 6,159,697, which are each incorporated herein by reference.)

In an exemplary embodiment, the anti-SMAD7 antisense therapy may be formulated in a pharmaceutically acceptable carrier and administered orally to a subject suffering from IBD.

Blood Sample

A blood sample from a subject may be obtained using techniques well-known in the art. Blood samples may include peripheral blood mononuclear cells (PMBCs) or RBC-depleted whole blood. PBMCs can be isolated from whole blood samples using different density gradient (e.g., Ficoll density gradient) centrifugation procedures. For example, whole blood (e.g., anticoagulated whole blood) is layered over the separating medium and centrifuged. At the end of the centrifugation step, the following layers are visually observed from top to bottom: plasma/platelets, PBMC, separating medium and erythrocytes/granulocytes. The PBMC layer may be collected and washed to remove contaminants.

Tissue Sample

A tissue sample from a subject (e.g., a tissue sample obtained from the small intestine and/or large intestine of a subject, e.g., a subject suffering from CD or UC) can be used as a source of cells, a source of RNA, a source of protein, or a source of thin sections for immunohistochemistry (IHC) for measuring the amount of CCR9+ FoxP3+ T cells, CCR9+ IFN-γ+ T cells, CCR9+ IL17A+ T cells, FoxP3+ T cells, IFN-γ+ T cells and/or IL17A+ T cells in the sample. The tissue sample can be obtained by using conventional biopsy instruments and procedures. Endoscopic biopsy, excisional biopsy and incisional biopsy are examples of recognized medical procedures that can be used by one of skill in the art to obtain gastrointestinal tissue samples. The tissue sample should be large enough to provide sufficient cells, RNA, protein, or thin sections for measuring marker gene (e.g., CCR9, FoxP3, IFN-γ, and/or IL17A) expression level or visualizing individual cells by flow cytometry, IHC, or ELISA, e.g., CCR9+ FoxP3+ T cell, CCR9+ IFN-γ+ T cell, CCR9+ IL17A+ T cell, FoxP3+ T cell, IFN-γ+ T cell and/or IL17A+ T cell expression.

The tissue sample can be in any form sufficient for cell sorting, RNA extraction, protein extraction, or preparation of thin sections. Accordingly, the tissue sample can be fresh, preserved through suitable cryogenic techniques, or preserved through non-cryogenic techniques. A standard process for handling clinical biopsy specimens is to fix the tissue sample in formalin and then embed it in paraffin. Samples in this form are commonly known as formalin-fixed, paraffin-embedded (FFPE) tissue. Suitable techniques of tissue preparation for subsequent analysis are well-known to those of skill in the art.

Flow Cytometry

Cell populations may be sorted based on cell surface markers by flow cytometry (e.g., fluorescence activated cell sorting (FACS) analysis). Methods for sorting and counting cells by FACS analysis are well-established and known to those of skill in the art. See, e.g., Robinson "Current Protocols in Cytometry" John Wiley & Sons Inc., New York. In general, cells obtained from a blood sample or a tissue sample may be prepared in a single cell suspension. Cells are then labeled with a fluorescent tag (e.g., a fluorescently labeled antibody to a cell surface marker present on the cell population(s) to be identified). The fluorescence can be direct or indirect. For direct fluorescence, a fluorescent tag (e.g., fluoroscein, rhodamine, or another fluorochrome) is covalently attached to a primary antibody. For indirect fluorescence, the primary antibody that binds to a marker present on the cell surface is not labeled with a fluorescent tag. The primary antibody is bound to the cell surface of the targeted cell population. Unbound antibody is removed by a washing step. A fluorescently-tagged secondary antibody that binds the primary antibody is added and any unbound antibody is removed by a washing step.

FACS analysis can be performed with live or fixed cells. FACS instruments are available to those skilled in the art and include FACScan, FACStar Plus, and FACSCalibur (Becton-Dickinson). FACS analysis software is available to those skilled in the art and includes FlowJo, CellQuest Pro (Becton-Dickinson), and WinMDI (Windows Multiple Document Interface for Flow Cytometry).

A person skilled in the art will appreciate that FACS analysis can be conducted with a single antibody or multiple antibodies for identifying, counting, and sorting distinct cell populations. For example, a cell population label with a single antibody can be detected and sorted from cells that do not express the specified marker (e.g., FoxP3+ T cell populations can be identified by an antibody specific for FoxP3; IFN-γ+ T cell populations can be identified by an antibody specific for IFN-γ; and IL17A+ T cell populations can be identified by an antibody specific for IL17A.)

A FACS instrument equipped with multiple lasers and fluorescence detectors allows for the use of multiple-antibody labeling and can precisely identify a target cell population. To achieve detection, cells can be labeled with multiple antibodies, each tagged with a different fluorescent label. For example, a blood sample may be simultaneously labeled with an APC-labeled mouse anti-human CCR9 antibody and a PE-labeled anti-human FoxP3 antibody for the detection of CCR9+ FoxP3+ T cell populations. In another embodiment, a tissue sample may be labeled with an APC-labeled mouse anti-human CCR9 antibody and an Alexa Fluor 647 mouse anti-human IL17A antibody for the detection of CCR9+ IL17A+ T cell population.

Exemplary antibodies that may be used to determine CCR9+ FoxP3+ T cell populations, CCR9+ IFN-γ+ T cell populations, and/or CCR9+ IL17A+ T cell populations by FACS analysis include fluorescent labeled antibodies against human CCR9, such as allophycocyanin (APC)-labeled mouse anti-human CCR9 antibody (R&D Systems, Catalog Numbers FAB 179A and FAB 1791A), Alexa Fluor® 647 mouse anti-human CCR9 antibody (BD Pharmigen, Catalog Number 557975), fluoroscein-labeled mouse anti-human CCR9 antibody (R&D Systems, Catalog Number FAB 179F), and phycoerythrin (PE)-labeled mouse anti-human CCR9 antibody (R&D Systems, Catalog Number FAB 179P).

Exemplary antibodies that may be used to determine FoxP3+ T cell populations and CCR9+ FoxP3+ T cell populations by FACS analysis include fluorescently labeled antibodies against human FoxP3, such as phycoerythrin (PE)-labeled anti-human FoxP3 antibody (Miltenyi Biotec, Catalog Number 130-093-014), allophycocyanin (APC)-labeled anti-human FoxP3 antibody (Miltenyi Biotec, Catalog Number 130-093-013), Alexa Fluor® 647 mouse anti-human FoxP3 antibody (BD Pharmigen, Catalog Number 560045), Alexa Fluor® 488 mouse anti-human FoxP3 antibody (AbD Serotec, Catalog Number MCA2376A488), and FITC-labeled mouse anti-human FoxP3 antibody (Abcam, Catalog Number ab93512).

Exemplary antibodies that may be used to determine IFN-gamma+ T cell populations and CCR9+ IFN-gamma+ T cell populations by FACS analysis include fluorescently labeled antibodies against human IFN-gamma such as FITC-labeled mouse anti-human IFN-gamma antibody (Abcam, Catalog Number ab47344), phycoerythrin (PE)-labeled mouse anti-human IFN-gamma antibody (Abcam, Catalog Number ab47345, and R&D Systems, Catalog Number IC285P), and fluoroscein-labeled mouse anti-human IFN-gamma antibody (R&D Systems, Catalog Number IC285F).

Exemplary antibodies that may be used to determine IL17A+ T cell populations and CCR9+ IL17A+ T cell populations by FACS analysis include fluorescently labeled antibodies against human IL17A such as Alexa Fluor 647 mouse anti-human IL17A antibody (eBioscience, Catalog Number 51-7179-42), phycoerythrin (PE)-labeled mouse anti-human IL17A antibody (R&D Systems, Catalog Number IC3171P), and allophycocyanin (APC)-labeled mouse anti-human IL17A antibody (R&D Systems, Catalog Number IC3171A).

Exemplary antibodies that may be used to determine CD103+ T cell populations and FoxP3+ CD103+ T cell populations by FACS analysis include fluorescently labeled antibodies against human CD103 such as phycoerythrin-labeled mouse anti-human integrin alpha E monoclonal antibody (Abcam, Catalog Number ab33267) and FITC-labeled mouse anti-human CD103 monoclonal antibody (AbD Serotec, Catalog Number MCA1416FT).

Exemplary antibodies that may be used to determine α4β7+ T cell populations by FACS analysis include fluorescently labeled antibodies against human α4β7, which are available from BD Biosciences.

In another embodiment, the amount of a cell population is determined by sorting the cells by flow cytometry and then measuring the amount of RNA encoding at least one marker selected from the group consisting of CCR9, FoxP3, IFN-gamma, and IL17A from the sorted cell population. Methods of RNA isolation and quantification are well-known in the art.

Immunohistochemistry

Distinct cell populations may be also determined by immunohistochemistry (IHC). Specifically, the number of CCR9+ FoxP3+ T cells, CCR9+ IFN-γ+ T cells, CCR9+ IL17A+ T cells, FoxP3+ T cells, IFN-γ+ T cells and/or IL17A+ T cells in a given cell population can be determined (e.g., visualized) by IHC. For example, assaying a CCR9+ FoxP3+ T cell population by IHC requires, for example, at least one antibody against a CCR9 protein, e.g., at least one anti-CCR9 antibody, and at least one antibody against a FoxP3 antibody, e.g., at least one anti-FoxP3 antibody. In exemplary embodiments, the anti-CCR9 antibody and the anti-FoxP3+ antibody are labeled with different labels, e.g., different fluorescent labels. In certain embodiments, the anti-CCR9 antibody and the anti-FoxP3 antibodies are different antibodies, e.g., mouse, rat, rabbit, etc., thus, providing for differential detection by labeled, e.g., fluorescent, secondary antibodies.

For IHC studies, for example, paraffin-embedded formalin fixed tissues samples can be sliced into sections, e.g., 5 micron sections. Typically, the tissue sections are initially treated in such a way as to retrieve the antigenic structure of proteins that were fixed in the initial process of collecting and preserving the tissue material. Slides are then blocked to prevent non-specific binding by the detection antibodies. The presence of, for example, CCR9, FoxP3, IFN-gamma, and/or IL17A proteins, is then detected by binding of the anti-CCR9, anti-FoxP3, anti-IFN-gamma, and/or anti-IL17A antibodies to the respective proteins. The detection (primary) antibody is linked to a fluorescent label, either directly or indirectly, e.g., through a secondary antibody or polymer that specifically recognizes the detection (primary) antibody. Typically, the tissue sections are washed and blocked with non-specific protein such as bovine serum albumin between steps. The samples may be counterstained with hematoxylin and/or eosin.

Anti-CCR9 antibodies suitable for IHC are commercially available, such as, for example, a goat anti-human CCR9 polyclonal antibody from Enzo Life Sciences (Catalog Number ALX-210-847-C200), a rabbit anti-human CCR9 polyclonal antibody from GenWay Biotech (Catalog Number 18-461-10269-0.05 ml), a CCR9 antibody from Novus Biologicals (Catalog Number NBP1-44201), and a mouse anti-human CCR9 monoclonal antibody from R&D Systems (Catalog Number MAB179).

Anti-FoxP3 antibodies suitable for IHC are commercially available, such as, for example, a rabbit anti-FoxP3 polyclonal antibody from Abbiotec (Catalog Number 250655), a goat anti-human FoxP3 polyclonal antibody from Abgent (Catalog Number AF1438a), a mouse anti-human FoxP3 monoclonal antibody from LifeSpan BioSciences (Catalog Number LS-C51576-40), and a mouse anti-human FoxP3 monoclonal antibody from MBL International (Catalog Number M120-3).

Anti-IFN-gamma antibodies suitable for IHC are commercially available, such as, for example, a rabbit anti-IFN-gamma polyclonal antibody from Abbiotec (Catalog Number 250707), a mouse anti-human IFN-gamma monoclonal antibody from BioLegend (Catalog Number 506512), a goat anti-human IFN-gamma monoclonal antibody from R&D Systems (Catalog Number AF-285-NA), and a rabbit anti-human IFN-gamma polyclonal antibody from Cell Sciences (Catalog Number CP2008).

Anti-IL17A antibodies suitable for IHC are commercially available, such as, for example, a rabbit anti-human IL17A polyclonal antibody from Proteintech Group (Catalog Number 13082-1-AP) and a goat anti-human IL17 polyclonal antibody from R&D Systems (Catalog Number AF-317-NA).

Anti-CD103 antibodies suitable for IHC are commercially available, such as, for example, a mouse anti-human integrin-alpha E monoclonal antibody from Abcam (Catalog Number ab33266) and a mouse anti-human CD103 monoclonal antibody from AbD Serotec (Catalog Number P38570).

Anti-integrin α4β7 antibodies are commercially available from BD Biosciences.

Cell-Based Enzyme-Linked Immunosorbent Assay

In some embodiments, cell populations may be identified by Enzyme-linked immunosorbent assay (ELISA). Specifically, CCR9+ FoxP3+ T cells, CCR9+ IFN-γ+ T cells, CCR9+ IL17A+ T cells, FoxP3+ T cells, IFN-γ+ T cells and/or IL17A+ T cells in a given cell population can be determined by, for example, a cell-based ELISA. For example, assaying a CCR9+ FoxP3+ cell population by ELISA requires at least one antibody against a CCR9 protein, e.g., at least one anti-CCR9 antibody, at least one antibody against a FoxP3 protein, e.g., at least one anti-FoxP3 antibody, and/or at least one secondary antibody, e.g. at least one labeled secondary antibody. In exemplary embodiments, the anti-CCR9 antibody and the anti-FoxP3 antibody are either not labeled or are labeled with different labels, e.g., different fluorescent labels. In certain embodiments, the anti-CCR9 antibody and the anti-FoxP3 antibodies are different antibodies, e.g., mouse, rat, rabbit, etc., thus, providing for differential detection by labeled, e.g., fluorescent or enzyme-linked, secondary antibodies.

Performing an ELISA, e.g., a cell-based ELISA, requires at least one capture antibody, at least one detection antibody, and/or at least one enzyme-linked or fluorescent labeled secondary antibody. For example, assaying a CCR9+ FoxP3+ cell population by the cell-based ELISA may require a polyclonal anti-CCR9 antibody as the capture antibody. The polyclonal anti-CCR9 antibody is immobilized on a solid support such as a polystyrene microtiter plate. Cells obtained from a blood sample or a tissue sample are then added and allowed to complex with the bound antibody. Unbound cells are removed with a wash. A detection antibody, e.g., a monoclonal anti-FoxP3 antibody, is added and is allowed to bind to the cells. The detection antibody is linked to an enzyme, either directly or indirectly, e.g., through a secondary antibody that specifically recognizes the detection antibody. Typically between each step, the plate, with bound cells, is washed with a wash buffer, e.g., a mild detergent solution. Typical ELISA protocols also include one or more blocking steps, which involve use of a non-specifically-binding protein such as bovine serum albumin to block unwanted non-specific binding of protein reagents to the plate. After a final wash step, the plate is developed by addition of an appropriate enzyme substrate, to produce a visible signal, which indicates the quantity of CCR9+ FoxP3+ cells in the sample. The substrate can be, e.g., a chromogenic substrate or a fluorogenic substrate.

ELISA methods, reagents and equipment are well-known in the art and commercially available.

Numerous anti-CCR9 antibodies suitable for ELISA are commercially available, such as, for example, an anti-CCR9 polyclonal antibody from Abcam (Catalog Number ab38567), a goat anti-human CCR9 polyclonal antibody from Enzo Life Sciences (Catalog Number ALX-210-847-C200), and a rabbit anti-human CCR9 polyclonal antibody from Novus Biologicals (Catalog Number H00010803-D01P).

Numerous anti-FoxP3 antibodies suitable for ELISA are commercially available, such as, for example, a rabbit anti-FoxP3 polyclonal antibody from Abbiotec (Catalog Number 250655), a goat anti-human FoxP3 polyclonal antibody from Abgent (Catalog Number AF1438a), and a mouse anti-human FoxP3 monoclonal antibody from LifeSpan BioSciences (Catalog Number LS-C82119-100).

Numerous anti-IFN-gamma antibodies suitable for ELISA are commercially available, such as, for example, a rabbit anti-IFN-gamma polyclonal antibody from Abbiotec (Catalog Number 250707), a mouse anti-human IFN-gamma monoclonal antibody from BioLegend (Catalog Number 507502), and a rabbit anti-human IFN-gamma polyclonal antibody from Cell Sciences (Catalog Number CP2008).

Anti-IL17A antibodies suitable for ELISA are commercially available, such as, for example, a rabbit anti-human IL17A polyclonal antibody from Proteintech Group (Catalog Number 13082-1-AP) and a goat anti-human IL17 monoclonal antibody from R&D Systems (Catalog Number MAB317).

Anti-CD103 antibodies suitable for ELISA are commercially available, such as, for example, a rabbit anti-human integrin alpha E antibody from Novus Biologicals (Catalog Number 36520002).

Anti-integrin α4β7 antibodies are commercially available from BD Biosciences.

In another embodiment, the amount of a cell population is determined by sorting the cells by flow cytometry and then measuring the amount of RNA encoding at least one marker selected from the group consisting of CCR9, FoxP3, IFN-gamma, and IL17A from the sorted cell population. Methods of RNA isolation and quantification are well-known in the art.

Control Samples

A control sample may include a sample (e.g., a blood or tissue sample) obtained from the subject prior to treatment with an anti-SMAD7 therapy. The control sample provides a baseline for monitoring a subject's progress to treatment. A control sample may be obtained from the subject on the day the anti-SMAD7 therapy is first administered (e.g., Day 1 of a treatment regimen). In other embodiments, a control sample may be obtained from a subject one day prior to the start of an anti-SMAD7 therapy (e.g., Day 0 of a treatment regimen). Alternatively, a control sample may be obtained from a subject 2, 3, 4, 5, 6, 7 or more days prior to the start of an anti-SMAD7 therapy. For example, the upregulation or down regulation of certain cell samples may be measured prior to treatment (e.g., a control sample), during treatment, and/or after treatment to monitor a subject's response to therapy, e.g., an anti-SMAD7 therapy.

In some embodiments, a control level may be established for a subject based on long-term monitoring of certain cell populations in the subject. In such instances, it is contemplated that a subject may undergo multiple rounds of treatment with an anti-SMAD7 therapy. The amount of a certain cell population detected following multiple rounds of treatment may be compared to a prior control level for the subject to determine whether the subject has responded to therapy and/or is likely to respond to further treatment with an anti-SMAD7 therapy. In other embodiments, a control or baseline level for a subject may be established based on an average measurement of a certain cell population determined from multiple baseline samples obtained over time (e.g., obtained over the course of weeks, months, or years). Accordingly, any test or assay conducted as disclosed herein may be compared with a previous or established control level and it may not be necessary to obtain a new control sample from the subject for comparison, e.g., if the subject is receiving more than one round of treatment with an anti-SMAD7 therapy.

Data Interpretation

A subject's responsiveness to treatment with an anti-SMAD7 therapy can be interpreted with respect to the control sample obtained from the subject prior to treatment. A subject may be identified as sensitive to treatment (e.g., responsive or likely to respond) to treatment with an anti-SMAD7 therapy if there is an increase in the amount of CCR9+ FoxP3+ T cells in the sample obtained from the subject, or a decrease in the amounts of CCR9+ IFN-gamma+ T cells, CCR9+ IL17A+ T cells, FoxP3+ T cells, IFN-γ+ T cells and/or IL17A+ T cells in the sample obtained from the subject compared to the control sample. The sample may be obtained at day 8 or later after initiation of therapy to determine sensitivity to treatment. In some embodiments, the sample may be obtained at 28, 56, and/or 84 days and/or longer. In other embodiments, the sample may be obtained after day 8, e.g., one week, two weeks, one month, two months, three months, six months, and/or one year or longer after the initiation of therapy to monitor sensitivity to treatment.

Alternatively, a subject may be identified as resistant to treatment (e.g., non-responsive or unlikely to respond) with an anti-SMAD7 therapy if there is a decrease in the amount of CCR9+ FoxP3+ T cells in the sample obtained from the subject, or a increase in the amounts of CCR9+ IFN-γ+ T cells, and/or CCR9+ IL17A+ T cells in the sample obtained from the subject compared to the control sample. The sample may be obtained at day 8 or later after initiation of therapy to determine resistance to treatment. In some embodiments, the sample may be obtained at day 28, 56, 84 or more days following initial treatment. In other embodiments, the sample may be obtained after day 8, e.g., one week, two weeks, one month, two months, three months, six months, and/or one year or longer after the initiation of therapy to monitor sensitivity to treatment.

Test Kits

The invention includes a test kit comprising certain components for performing the methods disclosed herein. A test kit may enhance convenience, speed and reproducibility in the performance of the disclosed assays. For example, an exemplary FACS-based test kit may include antibodies for identifying, sorting, and counting cells, e.g., anti-CCR9 antibodies, anti-FoxP3 antibodies, anti-IFN-gamma antibodies and/or anti-IL 17A antibodies. In other embodiments, the test kit contains not only antibodies, but also buffers, reagents and detailed instructions for identifying, sorting, and counting cells, using FACS technology. In some embodiments, the kit includes a test protocol and all the consumable components needed for the test, except the cell and/or tissue sample(s).

An exemplary IHC-based test kit may contain materials for determining cell populations by IHC. An IHC kit, for example, may contain a primary antibody against a CCR9 protein, e.g., a mouse anti-human CCR9 antibody, and a primary antibody against a FoxP3 protein, e.g., a mouse anti-human FoxP3 antibody, and a secondary antibody conjugated to a reporter enzyme, e.g., horseradish peroxidase. In other embodiments, the test kit contains not only antibodies, but also buffers, reagents and detailed instructions for identifying cell populations using IHC technology.

An exemplary ELISA-based test kit may contain materials for determining cell populations by ELISA. A cell-based ELISA kit, for example, may contain a capture antibody against a CCR9 protein, e.g., a rabbit anti-human CCR9 polyclonal antibody, and a detection antibody against a FoxP3 protein, e.g., a mouse anti-human FoxP3 monoclonal antibody, and/or a secondary antibody conjugated to a reporter enzyme, e.g., horseradish peroxidase. In other embodiments, the test kit contains not only antibodies, but also buffers, reagents and detailed instructions for identifying cell populations using the ELISA technology.

EXAMPLES

The invention is further illustrated by the following examples. The examples are provided for illustrative purposes only, and are not to be construed as limiting the scope or content of the invention in any way.

Example 1

Phase I Clinical Trial to Evaluate Safety and Efficacy of an Anti-SMAD7 Antisense Treatment in CD Patients Fifteen patients with active CD were enrolled in a phase I clinical trial to evaluate the safety and efficacy of an anti-SMAD7 antisense therapy for treating CD. Patients were initially screened from a group of 21 applicants and enrollees were assigned to one of three equally sized cohorts (FIG. 2). There were no significant differences in demographic or clinical characteristics among enrolled patients. However, patients of cohort 1 had a longer disease duration as compared with patients of the other two cohorts, and patients of cohorts 1 and 2 had more frequently undergone intestinal resection as compared to patients of cohort 3 (FIG. 3). The patients received 40 mg/day (N=5; Cohort I); 80 mg/day (N=5; Cohort 2); or 160 mg/day (N=5; Cohort 3) of GED-0301, an Smad7 antisense oligonucleotide (GTXGC-CCCTTCTCCCXGCAGC, wherein X is 5-methyl-2'-deoxycytidine 5' monophosphate (5-Me-dC) (SEQ ID NO: 6)) for 7 days.

Patients who met all the following criteria were be eligible for inclusion: 1.) Written informed consent, personally signed and dated by the patient prior any study-related procedure; 2.) Male or female patients between 18-45 years old; 3.) Female patients not of childbearing potential; female patients of childbearing potential upon negative pregnancy testing at screening and who use an effective method of birth control during the study; 4.) Patients with active CD at the time of the screening visit, defined as CDAI score of >220 and ≤400 for at least one week prior to enrollment; 5.) CD limited to terminal ileum and/or right colon; 6.) No treatment with anti TNF-α, other biologics, immunosuppressants (e.g., azathioprine, mercaptopurine, methotrexate), in the 90 days prior the enrollment; 7.) Patients with steroid resistance or steroid dependence; and 8.) Ability to understand and comply with study procedures and restrictions.

Subjects were excluded from the study if any of the following criteria were met: 1.) Pregnant or breastfeeding women; 2.) Patients with CD involving the stomach and/or the proximal small intestine or patients with lesions confined to the transverse and/or left colon; 3.) Use in the 90 days prior first dose of immunomodulators and biologics (e.g., azathioprine, mercaptopurine, methotrexate, infliximab, adalimumab natalizumab); 4.) Presence of local complications (e.g., abscesses, strictures and fistulae) dysplasia and malignancies, and extra-intestinal manifestations; 5.) Previous endoscopic balloon dilation, stricturoplasty or surgical resection for CD strictures; 6.) Patients underwent proctocolectomy; 7.) Any of the following laboratory alterations: APTT>1.5 Upper Limit of Normality (ULN); platelet count≤100,000/mm3; serum creatinine>1.5 ULN; total bilirubin>1.5 ULN (Excluding Gilbert Syndrome); AST and ALT>1.5 ULN; QTc interval>450 msec for males and >470 msec for females; 8.) Current or relevant previous history of serious, severe or unstable (acute or progressive) physical or psychiatric illness, including infections, malignancy, medical disorder that may require treatment (e.g., renal or hepatic impairment) or that makes the subject unlikely to fully complete the study, or any condition that presents undue risk from the study medication or procedures; 9.) Patients who smoke or otherwise consume tobacco products; 10.) History of alcohol or other substance abuse within the last year; 11.) Patients potentially presenting poor reliability (e.g., bad mental conditions); 12.) Known hypersensitivity to oligonucleotides or any ingredient in the study products; 13.) Patients who used another investigational agent or who took part in a clinical trial within the last 12 months days prior to randomization.

Safety of GED-0301 was daily evaluated by taking into account the followings: physical examinations, body weight (Kg), vital signs (systolic and diastolic blood pressure, heart rate, breath rate, body temperature), ECG (12 lead), collection of the AE and SAEs. Blood samples were checked for: haemoglobin, haematocrit, mean cell volume, red cell count, total and differential white cell count, MCH, platelet count, prothrombin time, activated partial thromboplastin time, creatinine, BUN, glucose, uric acid, proteins, bilirubins, alkaline phosphatase, CPK, AST, ALT, γ-GT, Na, K, cholesterol and triglycerides, complement activation (by monitoring Bb, C5a and C3a). An urinalysis (pH, ketones, leukocytes, protein, glucose, cyto-bacteriological examination) was also performed.

No consistent laboratory abnormalities or changes in vital signs were noted in any patient during the study. No significant increase in the serum levels of complement factors was documented. All the samples in the three cohorts yielded values below the lower limit of quantification, except one sample of a single patient from cohort 1 (patient 5, day 7, 6 hours), which gave a result of 11.2 ng/ml GED0301.

No serious adverse events were registered. Twenty-five adverse events (AE) were registered in 11 patients, with the most common events reported as mild (FIG. 4). Investigators rated AE as not related to treatment in 14 (56%) cases. Eleven out of these 14 AE, including laboratory abnormalities, were registered in 8 patients before drug administration. AE were considered unlikely to be related to the study drug in 12 cases (48%) and probably related to the study drug in one case (4%). This was an increase in the serum triglycerides count during the administration of the study drug. There was no apparent dose-response relationship in treatment-emergent AE. One patient of cohort 2 had a mild relapse of the disease on day 84, while another patient of cohort 3 experienced two severe episodes of abdominal pain and vomiting which required a daily treatment with steroids. One patient treated with 80 mg/day experienced high diastolic pressure on day 1, a few minutes after GED0301 administration and T wave inversion (in precordial leads) on day 84. After careful examination by cardiologists, both these AEs were considered secondary to the budesonide treatment received by the patient over the last months. An episode of allergic rhinitis was registered in one patient, with a history of allergic disease, on day 31. This AE resolved very quickly after a single administration of an antihistaminic compound.

An Independent Safety Committee (with expertise in toxicology, pharmacovigilance and clinical inflammatory bowel disease) was named to both monitor and evaluate the safety parameters. On day 1 and day 7, blood samples were also taken at 0, 2, 6, 12 and 24 hours post dosing, for pharmacokinetic analysis and for peripheral blood mononuclear cell (PBMC) isolation. Efficacy of treatment was established by evaluating at different time points (e.g., day 8, 28, 60, and 90) the number of patients who fulfilled the remission criteria (CDAI<150) or achieved a clinical response defined as a 70-point or greater decrease from baseline in CDAI score.

Example 2

SMAD7 is Expressed in Human Intestinal Follicles and Peyer's Patches

Intestinal samples were available from four CD patients undergoing surgical resection for a chronically active disease and who respond poorly to medical treatment. These samples were used for analysis of SMAD7 by immunohistochemistry.

Tissue sections from patients with CD were cut, deparaffinized, and dehydrated through xylene and ethanol. For the purpose of antigen retrieval, the slides were incubated in a microwave oven for 10 minutes in 0.01 M citrate buffer, pH 6. To block endogenous peroxidase, the slides were then incubated in 2% $H_2O_2$ for 20 minutes at room temperature. Incubation with a mouse anti-human SMAD7 antibody was performed at room temperature for 1 hour. After rinsing in Tris-buffered saline, slides were incubated with a rabbit anti-mouse antibody conjugated to horseradish peroxidase for 30 minutes at room temperature Immunoreactive cells were visualized by addition of diaminobenzadine as substrate and lightly counterstained with hematoxylin. As a negative control, tissue sections were processed using purified, normal rabbit anti-serum instead of the primary SMAD7 antibody.

These studies showed that SMAD7 is expressed in human intestinal follicles and Peyer's Patches (FIG. 5). This observation suggests that down regulation or knock-down of SMAD7 with SEQ ID NO: 6 may allow TGF-beta1 to act in these structures, thus, reducing the fraction of T cells expressing inflammatory cytokines (e.g., IFN-gamma) and enhancing the percentage of regulatory T cells (which are referred to herein as Tregs).

Example 3

Anti-SMAD7 Antisense Oligonucleotide Treatment Modulates Expression of Inflammatory Cytokines in Cultured T Cells The effects of GED0301 on the expression of inflammatory cytokines in cultured CCR9-positive cells were investigated. To determine the effect of GED0301 exposure on CCR9-positive cells, PBMCs, isolated from five active steroid-dependent CD patients who were not enrolled in the trial, were resuspended in X-vivo serum-free culture medium (Lonza, Verviers, Belgium), supplemented with penicillin (100 U/ml) and streptomycin (100 U/ml), and cultured in the presence or absence of Smad7 antisense (GED0301) or sense oligonucleotide (2 µg/ml) for 48 hours. Both Smad7 antisense and sense oligonucleotides were combined with Lipofectamine 2000 (Invitrogen, Carlsbad, Calif.) to facilitate efficient transfection of cultured cells. Cells were stained and analyzed by flow cytometry using antibodies directed against CCR9, β7, IFN-γ, and IL17A in order to determine the percentage of T cells that express either IFN-γ or IL17A within the CCR9+ or β7+ populations under each treatment condition.

Figure 6:
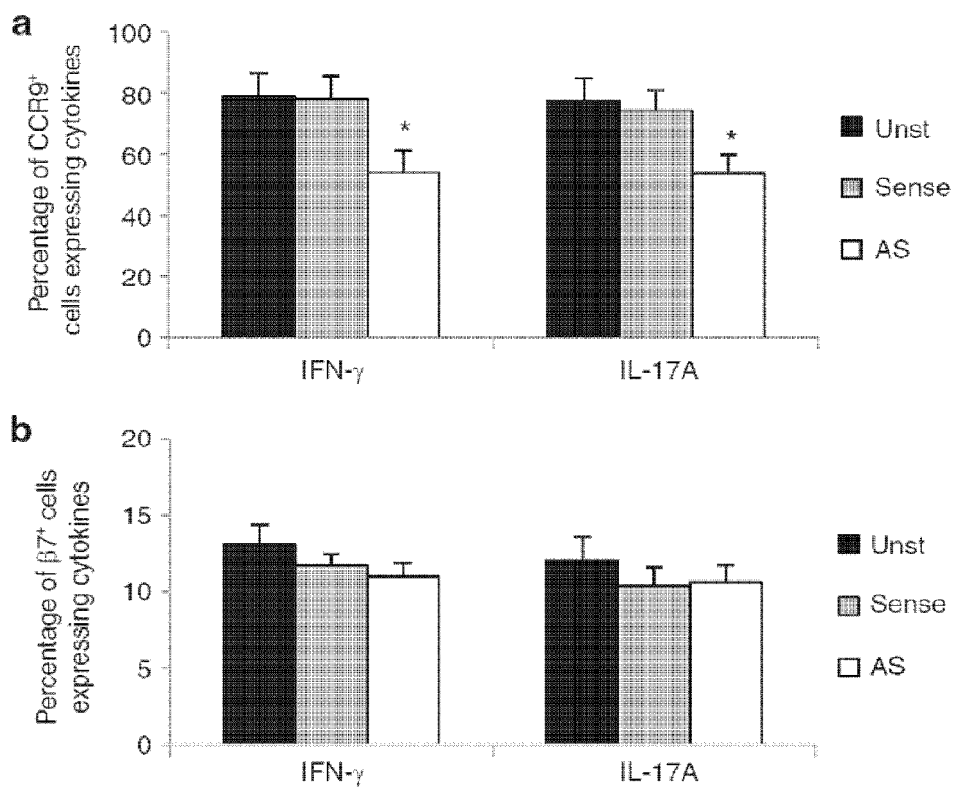
FIG. 6 shows the effect of isolated PBMCs from CD patients left unstimulated (Unst) or treated with Smad7 sense (Sense) or GED0301 (AS) oligonucleotides on the percent of IFN-γ or IL-17A cells within the (A) CCR9+ or (B) β7+ populations.

The expression of IFN-γ and IL17A in the CCR9+ and β7+ populations from the above cultured PBMCs was analyzed in order to determine whether GED0301 directly inhibits the expression of inflammatory cytokines in CCR9+ cells. Treatment of CD PBMCs with GED0301 (Smad7 antisense) significantly reduced the percentages of IFN-γ and IL-17A-expressing CCR9+ cells (FIG. 6A), while the fraction of cytokine-expressing β7+ cells remained unchanged (FIG. 6B). For example, the percentage of CCR9+ cells expressing IFN-γ was 78.9±7.3 in the untreated cells; 78.3±7.3 in the cells treated with the sense strand; and 54±7.2 in the cells treated with GED0301. Similarly, the percentage of CCR9+ cells expressing IL-17A was 77.4±7.3 in the untreated cells; 74.3±6.4 in the cells treated with the sense strand; and 53.9±5.7 in the cells treated with GED0301. In contrast, the percentages of untreated, sense-treated and GED0301-treated β7+ cells expressing IFN-γ were 13.1±1.2; 11.7±0.7, and 11±0.8, respectively, and the percentages of untreated, sense-treated and GED0301-treated β7+ cells expressing IL-17A were 12.1±1.5; 10.4±1.2, and 10.6±1.1. Thus, direct exposure of cultured CCR9+ CD PBMCs to GED0301 results in decreased expression of inflammatory cytokines.

Example 4

Anti-SMAD7 Antisense Oligonucleotide Treatment Modulates Expression of T Cell Populations This Example describes a study investigating the fraction of circulating CCR9+ FoxP3+ T cells, CCR9+ IFN-γ+ T cells, CCR9+ IL17A+ T cells, FoxP3+ T cells, IFN-γ+ T cells, IL17A+ T cells, FoxP3+ CD103+ T cells and integrin α4β7+ T cells as the activation status of these Treg cell populations reflect the immune response occurring in the follicles and Peyer's Patch of the intestines. In the studies described below, for each cohort tested, T cell populations were measured at Day 0 to determine a baseline measurement for each patient. GED-0301 was administered as described above in Example 1 for 7 days and T cell populations were measured again at Day 8, Day 28, and for some cell populations at Day 84.

The manipulation of the peripheral pool of Tregs has been a particular focus for the treatment of immuno-mediated diseases and transplantation. Previous studies have shown that the number of peripheral blood Tregs can be increased by anti-TNF alpha antibodies, and that increases are only seen in patients who respond to anti-TNF alpha therapies. The effect of anti-TNF alpha therapy on Tregs may be mediated by TGF-beta1.

The effect of SMAD7 antisense oligonucleotide therapy was investigated to determine whether SMAD7 antisense oligonucleotide therapy positively regulates the number of Tregs as a result of enhanced TGF-beta1 activity. The effect of SMAD7 antisense therapy was also studied to determine whether such treatment leads to changes in the number of circulating FoxP3+ Tregs and if this effect is associated with changes in the percentages of effector Th1/Th17 cells.

In addition, CCR9+ T cells are enriched in the peripheral circulation of patients with Crohn's disease and have mucosal T cell characteristics, including an activation phenotype, responsiveness to CD2 activation, and the ability to make both inflammatory (e.g., IFN-gamma) and regulatory (e.g., IL10) cytokines. The effect of SMAD7 antisense therapy was also studied to determine whether such treatment leads to changes in the number of circulating CCR9+ cells.

For PBMC isolation and flow-cytometry analysis, blood samples (10 mg) were collected in heparin-containing tubes, diluted with RPMI 1640 (1:1) and separated by density gradient centrifugation using Ficoll-Paque. For this purpose, tubes were centrifuged at 1800 rpm for 30 minutes, and the resulting PBMCs were collected and washed in RPMI1640 twice.

PBMCs were resuspended in RPMI 1640 supplemented with 10% inactivated FBS, penicillin (100 U/ml), and streptomycin (100 mg/ml). Cells were phenotypically characterized by flow cytometry using the following antibodies: APC-labeled anti-human CCR9 and PE-labeled anti-human Foxp3. All antibodies were used at 1:50 final dilution.

PBMCs were also seeded in 96-well U-bottom culture dishes, and stimulated with Phorbol 12-myristate 13-acetate (PMA, 10 ng/ml), ionomycin (1 mg/ml), and brefeldin A (10 mg/ml). After 5 hours, cells were stained for CCR9 expression using the above antibodies as well as for IFN-gamma and IL-17A using the following antibodies: FITC anti-human IFN-gamma antibody, Alexa Fluor 647 anti-human IL-17A antibody, and PE-anti-human IL17A antibody. All antibodies were used at 1:50 final dilution. Appropriate isotype-matched controls were included in all of the experiments. The FITC anti-human IFN-gamma antibody was obtained from Beckton Dickinson and all the other antibodies, used herein were obtained from EBiosciences.

Values are expressed as median and differences between groups were compared using the Mann Whitney U test. Statistical significance ($p<0.05$) was determined using the Wilcoxon matched pairs test.

The effects of GED0301 treatment on the fraction of inflammatory/counter-regulatory lymphocytes were investigated. GED0301 treatment did not significantly alter the percentage of circulating CD3+, CD4+, CD8+, CD25+, CD161+, CD62L+, α4β7+, or CCR9+ cells as monitored on days 8 and 28 of the trial (FIG. 7). Similarly, no significant changes were observed in the fraction of interleukin (IL)-17A+ cells, IL-10+ cells, FoxP3+ cells, interferon (IFN)-γ- and IL-17A-expressing α4β7+ cells, or FoxP3-expressing CD103+ cells following GED0301 treatment.

Tables I and Ia show the results of Cohort 1, which received 40 mg of GED-0301/day for 7 days. Table I shows the percentage of a given T cell population in the total cell population at Days 0, 8, 28. Table Ia shows the percentage of CCR9+ FoxP3+ T cells, FoxP3+ T cells and CD103+ FoxP3+ T cells in the total cell population at Days 0, 8, 28 and 84.

Table II shows the results of Cohort 2, which received 80 mg of GED-0301/day for 7 days. Table II shows the percentage of a given T cell population in the total cell population at Days 0, 8, and 28. Table IIa shows the percentage of CCR9+ FoxP3+ T cells, FoxP3+ T cells and CD103+ FoxP3+ T cells in the total cell population at Days 0, 8, 28 and 84.

Table III shows the results of Cohort 3, which received 160 mg of GED-0301/day for 7 days. Table III shows the percentage of a given T cell population in the total cell population at Days 0, 8, and 28. Table Ma shows the percentage of CCR9+ FoxP3+ T cells, FoxP3+ T cells and CD103+ FoxP3+ T cells in the total cell population at Days 0, 8, 28 and 84.

Table IV shows the combined results of the total patients from Cohorts 1-3. Table IV shows the percentage of a given T cell population in the total cell population at Days 0, 8, and 28. Table IVa shows the percentage of CCR9+ FoxP3+ T cells, FoxP3+ T cells and CD103+ FoxP3+ T cells in the total cell population at Days 0, 8, 28 and 84.

TABLE I

| Cell population | Day 0 | | | Day 8 | | | Day 28 | | |
| --- | --- | --- | --- | --- | --- | --- | --- | --- | --- |
| | Median | Max. | Min. | Median | Max. | Min. | Median | Max. | Min. |
| CCR9+ IFN-g+ | 1.5% | 3.25% | 0.70% | 0.3% | 1.6% | 0.13% | 0.80% | 0.85% | 0.40% |
| CCR9+ IL-17A+ | 0.28% | 2.8% | 0.02% | 0.44% | 2.7% | 0.05% | 0.15% | 0.90% | 0.00% |
| CCR9+ FoxP3+ | 0.07% | 0.20% | 0.01% | 0.25% | 0.70% | 0.02% | 0.18% | 0.21% | 0.10% |
| IFN-g+ | 14.5% | 22.99% | 6.29% | 7.97% | 13.82% | 3.5% | 11.00% | 27.00% | 4.95% |
| IL-17A+ | 1.4% | 2.50% | 0.4% | 1.2% | 2.80% | 0.64% | 1.02% | 4.70% | 0.30% |
| FoxP3+ | 0.80% | 2.20% | 0.19% | 0.90% | 2.50% | 0.21% | 1.50% | 3.20% | 0.20% |
| FoxP3+ CD103+ | 0.18% | 4.60% | 0.03% | 0.30% | 0.40% | 0.07% | 0.28% | 0.80% | 0.10% |
| integrin α4β7+ | 2.70% | 2.90% | 2.30% | 1.35% | 2.40% | 0.51% | 0.99% | 2.60% | 0.73% |

TABLE Ia

| Cell pop. | Day 0 | | | Day 8 | | | Day 28 | | | Day 84 | | |
|---|---|---|---|---|---|---|---|---|---|---|---|---|
| | Med. | Max. | Min. | Med. | Max. | Min. | Med. | Max. | Min. | Med. | Max. | Min. |
| CCR9+ FoxP3+ | 0.07% | 0.20% | 0.01% | 0.25% | 0.70% | 0.02% | 0.18% | 0.21% | 0.10% | 0.46% | 2.50% | 0.01% |
| FoxP3+ | 0.80% | 2.20% | 0.19% | 0.90% | 2.50% | 0.21% | 1.50% | 3.20% | 0.20% | 1.06% | 2.8% | 0.05% |
| FoxP3+ CD103+ | 0.18% | 4.60% | 0.03% | 0.30% | 0.40% | 0.07% | 0.28% | 0.80% | 0.10% | 0.28% | 1.2% | 0.05% |

TABLE II

| Cell population | Day 0 | | | Day 8 | | | Day 28 | | |
|---|---|---|---|---|---|---|---|---|---|
| | Median | Max. | Min. | Median | Max. | Min. | Median | Max. | Min. |
| CCR9+ IFN-g+ | 1.40% | 14.00% | 0.40% | 1.00% | 5.20% | 0.50% | 9.40% | 20.00% | 0.56% |
| CCR9+ IL-17A+ | 0.80% | 9.80% | 0.28% | 0.3% | 5.20% | 0.09% | 1.21% | 4.50% | 0.40% |
| CCR9+ FoxP3+ | 0.50% | 0.60% | 0.20% | 0.40% | 0.50% | 0.20% | 0.40% | 0.50% | 0.16% |
| IFN-g+ | 9.80% | 20.90% | 4.80% | 5.70% | 34.00% | 1.70% | 14.95% | 34.00% | 4.50% |
| IL-17A+ | 0.70% | 5.80% | 0.20% | 0.19% | 4.60% | 0.00% | 1.00% | 4.60% | 0.22% |
| FoxP3+ | 1.70% | 2.30% | 0.60% | 1.10% | 1.60% | 0.80% | 0.80% | 1.60% | 0.60% |
| FoxP3+ CD103+ | 0.20% | 0.40% | 0.12% | 0.23% | 0.34% | 0.14% | 0.34% | 0.06% | 0.07% |
| integrin α4β7+ | 2.40% | 4.20% | 0.92% | 3.29% | 7.00% | 1.40% | 3.38% | 4.80% | 1.10% |

TABLE IIa

| Cell pop. | Day 0 | | | Day 8 | | | Day 28 | | | Day 84 | | |
|---|---|---|---|---|---|---|---|---|---|---|---|---|
| | Med. | Max. | Min. | Med. | Max. | Min. | Med. | Max. | Min. | Med. | Max. | Min. |
| CCR9+ FoxP3+ | 0.50% | 0.60% | 0.20% | 0.40% | 0.50% | 0.20% | 0.40% | 0.50% | 0.16% | 0.60% | 5.00% | 0.10% |
| FoxP3+ | 1.70% | 2.30% | 0.60% | 1.10% | 1.60% | 0.80% | 0.80% | 1.60% | 0.60% | 1.80% | 4.00% | 0.15% |
| FoxP3+ CD103+ | 0.20% | 0.40% | 0.12% | 0.23% | 0.34% | 0.14% | 0.34% | 0.06% | 0.07% | 0.20% | 1.10% | 0.10% |

TABLE III

| Cell population | Day 0 | | | Day 8 | | | Day 28 | | |
|---|---|---|---|---|---|---|---|---|---|
| | Median | Max. | Min. | Median | Max. | Min. | Median | Max. | Min. |
| CCR9+ IFN-g+ | 14.00% | 35.00% | 2.80% | 8.00% | 16.00% | 0.40% | 10.30% | 31.00% | 1.30% |
| CCR9+ IL-17A+ | 4.40% | 7.80% | 3.50% | 4.00% | 8.00% | 0.30% | 1.50% | 280.00% | 1.00% |
| CCR9+ FoxP3+ | 0.80% | 1.20% | 0.10% | 1.30% | 1.90% | 0.70% | 0.70% | 1.5% | 0.28% |
| IFN-g+ | 10.80% | 26.00% | 3.60% | 8.50% | 15.00% | 1.70% | 13.00% | 29.00% | 3.40% |
| IL-17A+ | 2.10% | 3.60% | 1.00% | 1.20% | 5.30% | 1.10% | 1.50% | 5.60% | 0.80% |
| FoxP3+ | 2.80% | 3.30% | 1.70% | 2.10% | 4.60% | 1.60% | 1.50% | 4.40% | 0.80% |
| FoxP3+ CD103+ | 0.80% | 1.20% | 0.20% | 0.70% | 1.80% | 0.50% | 0.70% | 1.40% | 0.24% |
| integrin α4β7+ | 2.80% | 6.30% | 2.50% | 1.10% | 6.80% | 0.60% | 3.50% | 5.20% | 0.90% |

TABLE IIIa

| Cell pop. | Day 0 | | | Day 8 | | | Day 28 | | | Day 84 | | |
|---|---|---|---|---|---|---|---|---|---|---|---|---|
| | Med. | Max. | Min. | Med. | Max. | Min. | Med. | Max. | Min. | Med. | Max. | Min. |
| CCR9+ FoxP3+ | 0.80% | 1.20% | 0.10% | 1.30% | 1.90% | 0.70% | 0.70% | 1.5% | 0.28% | 0.40% | 0.8% | 0.12% |
| FoxP3+ | 2.80% | 3.30% | 1.70% | 2.10% | 4.60% | 1.60% | 1.50% | 4.40% | 0.80% | 0.40% | 8.49% | 0.23% |
| FoxP3+ CD103+ | 0.80% | 1.20% | 0.20% | 0.70% | 1.80% | 0.50% | 0.70% | 1.40% | 0.24% | 0.20% | 1.40% | 0.10% |

TABLE IV

| | Day 0 | | | Day 8 | | | Day 28 | | |
|---|---|---|---|---|---|---|---|---|---|
| Cell population | Median | Max. | Min. | Median | Max. | Min. | Median | Max. | Min. |
| CCR9+ IFN-g+ | 2.8% | 35.00% | 0.40% | 1.0% | 16.00% | 0.13% | 5.05% | 31.00% | 0.40% |
| CCR9+ IL-17A+ | 2.8% | 9.8% | 0.02% | 0.44% | 8.00% | 0.05% | 1.00% | 280.00% | 0.00% |
| CCR9+ FoxP3+ | 0.20% | 1.20% | 0.01% | 0.50% | 1.90% | 0.02% | 0.40% | 4.00% | 0.10% |
| IFN-g+ | 10.60% | 26.00% | 3.60% | 7.2% | 34.00% | 1.70% | 13.00% | 34.00% | 3.40% |
| IL-17A+ | 1.4% | 5.80% | 0.20% | 1.10% | 5.30% | 0.00% | 1.06% | 5.60% | 0.22% |
| FoxP3+ | 1.70% | 3.30% | 0.19% | 1.23% | 4.60% | 0.21% | 1.25% | 4.40% | 0.20% |
| FoxP3+ CD103+ | 0.20% | 4.60% | 0.03% | 0.34% | 1.80% | 0.07% | 0.34% | 1.40% | 0.07% |
| integrin α4β7+ | 2.70% | 6.30% | 0.92% | 2.00% | 7.00% | 0.51% | 2.60% | 5.2% | 0.073% |

TABLE IVa

| | Day 0 | | | Day 8 | | | Day 28 | | | Day 84 | | |
|---|---|---|---|---|---|---|---|---|---|---|---|---|
| Cell pop. | Med. | Max. | Min. | Med. | Max. | Min. | Med. | Max. | Min. | Med. | Max. | Min. |
| CCR9+ FoxP3+ | 0.20% | 1.20% | 0.01% | 0.50% | 1.90% | 0.02% | 0.40% | 4.00% | 0.10% | 0.46% | 5.00% | 0.01% |
| FoxP3+ | 1.70% | 3.30% | 0.19% | 1.23% | 4.60% | 0.21% | 1.25% | 4.40% | 0.20% | 1.06% | 8.49% | 0.50% |
| FoxP3+ CD103+ | 0.20% | 4.60% | 0.03% | 0.34% | 1.80% | 0.07% | 0.34% | 1.40% | 0.07% | 0.20% | 1.40% | 0.02% |

As shown in each of the tables above, a significant decrease of T cell populations expressing CCR9+ IFN-γ+ was observed at day 8 (e.g., Table IV shows 2.8% expression at day 0 and 1.0% expression at day 8; see FIG. 8B).

A decrease CCR9+ IL17A+ T cell populations was also observed (e.g., Table IV shows 2.8% expression at day 0 and 0.44% expression at day 8; see FIG. 8D). A significant decrease from Day 0 was also observed at Day 28 in CCR9+ IL17A+ T cell populations (e.g., Table IV shows 1.00% expression at Day 28; see FIG. 8D). The decrease was still present at day 84 (median expression 1%; range 0.08%-4.8%).

An increase in CCR9+ FoxP3+ T cell populations was observed at Day 8 through day 84 (e.g., Table IV shows 0.2% expression at day 0 and 0.5% expression at day 8; see FIG. 8F).

A significant decrease in IFN-γ+ T cell populations was observed at day 8 (e.g., Table IV shows 10.6% expression at day 0 and 7.2% expression at day 8; see FIG. 8A).

A decrease of IL17A+ T cell populations was also observed (e.g., Table IV shows 1.4% expression at day 0 and 1.1% expression at day 8; see FIG. 8C).

A decrease in FoxP3+ T cell populations was also observed on day 8 (e.g., Table IV shows 1.7% expression at day 0 and 1.23% expression at day 8; see FIG. 8E).

No change in FoxP3+CD103+ T cell populations (e.g., Table IV shows 0.2% expression at day 0 and 0.34% expression at day 8) and integrin α4β7 T cell populations (e.g., Table IV shows 2.7% expression at day 0 and 2% expression at day 8) were observed.

The results shown in Tables I-IV demonstrate that inhibition of SMAD7 with GED-0301 in CD patients modulates the expression of specific T cell populations. In particular, we observed a down-regulation of CCR9+ IFN-γ+ T cell, CCR9+ IL17A+ T cell, FoxP3+ T cell, IFN-γ+ T cell, and IL17A+ T cell populations following GED-0301 treatment at day 8 and an upregulation of CCR9+ FoxP3+ T cell populations following GED-0301 treatment at day 8. CCR9+ IL17A+ T cell populations were also down regulated following GED-301 treatment at Day 28 (e.g., when compared to Day 0). The results shown in Tables I-IV suggest that inhibition of SMAD7 with GED-0301 in CD patients reduces the synthesis of Th1 cytokines and restores the susceptibility of effector T cells to the regulatory T cells (Tregs)-mediated immunosuppression. This is consistent with the demonstration that TGF-beta1 is a powerful inhibitor of Th1 cell responses, and a key mediator of the peripheral differentiation and activity of T regs.

CDAI scores were also measured for patients in each of the three cohorts discussed above. Baseline CDAI scores were measured at Day 0, and measured again on Days 1, 4, 8, 28, and 84 of treatment. Tables V-VII provide the CDAI scores of representative patients for each of Cohorts 1-3, respectively.

X. As shown in Table V below, patients in Cohort 1, who received 40 mg of GED-0301 for 7 days, showed a decrease in CDAI score by day 4 of treatment that was maintained throughout the monitoring period (Day 84).

TABLE V

| Patients (Cohort 1) | Baseline | Day 1 | Day 4 | Day 8 | Day 28 | Day 84 |
|---|---|---|---|---|---|---|
| Patient 1-01 | 289 | 278 | 154 | 42 | 119 | 89 |
| Patient 1-02 | 253 | 257 | 181 | 86 | 93 | 154.4 |
| Patient 1-03 | 221 | 204 | 138 | 89 | 45 | 35 |
| Patient 1-04 | 302 | 294 | 203 | 41 | 18 | 81 |
| Patient 1-05 | 306 | 331 | 275 | 163 | 144 | 167 |

As shown in Table VI below, patients in Cohort 2, who received 80 mg of GED-0301 for 7 days, showed a decrease in CDAI score by day 4 of treatment that was maintained throughout the monitoring period (Day 84).

TABLE VI

| Patients (Cohort 2) | Baseline | Day 1 | Day 4 | Day 8 | Day 28 | Day 84 |
|---|---|---|---|---|---|---|
| Patient 2-08 | 299 | 293 | 224 | 70 | 119.4 | 73 |
| Patient 2-09 | 400 | 401 | 322.2 | 215 | 301 | 339 |
| Patient 2-10 | 268 | 330 | 213 | 126 | 213.5 | 225 |
| Patient 2-11 | 287 | 299.8 | 207 | 95.6 | 52 | 46 |
| Patient 2-12 | 252 | 226 | 194 | 154 | 133 | 185 |

As shown in Table VII below, patients in Cohort 3, who received 160 mg of GED-0301 for 7 days, showed a decrease in CDAI score by day 4 of treatment that was maintained throughout the monitoring period (Day 84).

TABLE VII

| Patients (Cohort 3) | Baseline | Day 1 | Day 4 | Day 8 | Day 28 | Day 84 |
|---|---|---|---|---|---|---|
| Patient 3-15 | 230 | 210 | 168.6 | 44 | 31 | 145 |
| Patient 3-16 | 260 | 217 | 133 | 53 | 71 | 94 |
| Patient 3-17 | 292 | 279 | 219 | 113 | 88 | 184 |
| Patient 3-18 | 290 | 280 | 242 | 95 | 71 | 118 |
| Patient 3-19 | 257 | 240 | 155 | 37 | 49 | 134 |

Figures 8, 9:
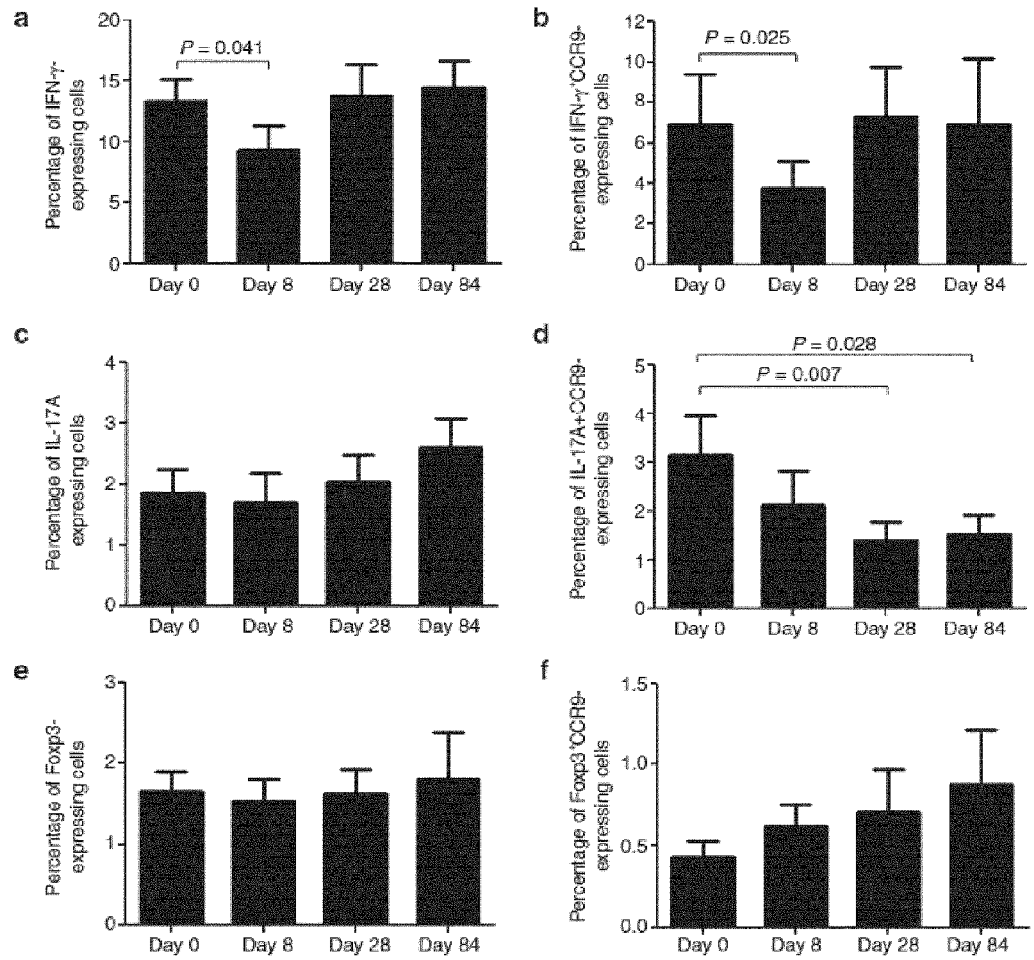
FIG. 8 displays graphs showing the percentage of (A) IFN-γ+, (B) IFN-γ+CCR9+, (C) IL-17A+, (D) CCR9+ IL-17A+, (E) FoxP3+, and (F) FoxP3+CCR9+ T cells after 0, 8, 28 and 84 days.
FIG. 9 shows the average CDAI values at baseline, day 8, and day 28 of the trial for each cohort as well as the average CDAI values at each timepoint for the entire group of patients.

The results in Tables V-VII demonstrate that treatment with GED-0301 reduces the CDAI scores of patients suffering from Crohn's disease. At enrollment, the median Crohn's disease activity index (CDAI) score of all patients was 287 (221-400) (FIG. 9). The median CDAI score was 289 (range 221-306) for patients of cohort 1, 287 (range 252-400) for patients of cohort 2 and 287 (range 221-400) for patients of cohort 3. In all three cohorts, the patients responded to treatment (e.g., a 70 point or greater decrease from baseline CDAI score was observed for each patient), such that at day 8, all 15 patients displayed a decrease in CDAI score and 12/15 patients from Cohorts 1-3 entered remission (i.e., CDAI score<150). (Table V-VII). Specifically, 4/5 patients of cohort 1, 3/5 patients of cohort 2 and 5/5 patients of cohort 3 had a CDAI score<150 (Tables V-VII). At day 28, clinical response was evident in all 15 patients as well (Table V-VII) and there was a significant decrease of CDAI score from baseline (P<0.0001). Clinical remission at day 28 was registered in 13/15 patients (86%) (5/5 of cohort 1, 3/5 of cohort 2 and 5/5 of cohort 3) (Table V-VII). At day 84, the total CDAI score was significantly lower than that measured at baseline (Table V-VII, P<0.0001) and 9/15 (60%) patients were still in remission. In particular, this was seen in 3 patients of cohort 1, 2 patients of cohort 2, and 4 patients of cohort 3 (Table V-VII). A significant decrease of CDAI score from baseline to day 8, 28 and 84 was seen even when analysis was performed in each cohort (FIG. 9). The results suggest that there is a correlation between induction of remission and/or improved outcome and T cell subpopulations. In addition, the CDAI scores observed at Day 84 show an increase from earlier time points (e.g., days 8 and 28), which was consistent with corresponding fluctuations in certain T cell populations at Day 84 (e.g., CCR9+ FoxP3+ T cell populations increased from Day 0 to Day 8, but at Day 84, this population of T cells appears to decrease).

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

What is claimed is:

1. A method of treating Inflammatory Bowel Disease (IBD) in a subject in need thereof, the method comprising administering an anti-SMAD7 therapy to a subject who has been
   determined to have an increased amount of a cell population of CCR9+ FoxP3+ cells, and/or a decreased amount of at least one cell population selected from the group consisting of CCR9+ IFN-gamma+ T cells, CCR9+ IL17A+ T cells, FoxP3+ T cells, IFN-gamma+ T cells, and IL17A+ T cells, relative to a known control level of the corresponding cell population, in response to administration of the anti-SMAD7 therapy.

2. The method of claim 1, wherein the subject has been determined to have two or more of the following:
   an increase in the amount of CCR9+ FoxP3+ T cells that indicates that the subject is likely to respond, or is responsive, to the anti-SMAD7 therapy;
   a decrease in the amount of CCR9+ IFN-gamma+ T cells that indicates that the subject is likely to respond, or is responsive, to the anti-SMAD7 therapy;
   a decrease in the amount of CCR9+ IL17A+ T cells that indicates that the subject is likely to respond, or is responsive, to the anti-SMAD7 therapy;
   a decrease in the amount of FoxP3+ T cells that indicates that the subject is likely to respond, or is responsive, to the anti-SMAD7 therapy;
   a decrease in the amount of IFN-gamma+ T cells that indicates that the subject is likely to respond, or is responsive, to the anti-SMAD7 therapy;
   a decrease in the amount of IL17A+ T cells that indicates that the subject is likely to respond, or is responsive, to the anti-SMAD7 therapy.

3. The method of claim 1, wherein the increase or the decrease in the amount of the cell population is determined by a method carried out in vitro.

4. The method of claim 1, wherein the Inflammatory Bowel Disease (IBD) is Crohn's disease (CD) and/or ulcerative colitis (UC).

5. The method of claim 1, wherein the increase in the amount of CCR9+ FoxP3+ T cells, and/or the decrease in the amount of CCR9+ IFN-gamma+ T cells, the decrease in the amount of CCR9+ IL17A+ T cells, the decrease in the amount of FoxP3+ T cells, the decrease in the amount of IFN-gamma+ T cells, or the decrease in the amount of IL17A+ T cells indicates that the subject is likely to enter remission.

6. The method of claim 1, wherein the increase or the decrease in the amount of the cell population is determined by flow cytometry, by immunohistochemistry, and/or by RNA/DNA analysis.

7. The method of claim 6, wherein flow cytometry and/or the immunohistochemistry is performed using an antibody selected from the group consisting of: an anti-CCR9 antibody, an anti-FoxP3 antibody, an anti-IFN-gamma antibody, and an anti-IL17A antibody.

8. The method of claim 1, wherein the control level is a baseline level of the corresponding cell population obtained from the subject prior to administration of the anti-SMAD7 therapy, or obtained immediately after the administration of the anti-SMAD7 therapy.

9. The method of claim 8, wherein the anti-SMAD7 therapy is an anti-SMAD7 antisense therapy.

10. The method of claim 9, wherein the anti-SMAD7 antisense therapy is an anti-SMAD7 antisense oligonucleotide comprising the antisense oligonucleotide sequence of SEQ ID NO: 4, SEQ ID NO: 5, SEQ ID NO: 6, SEQ ID NO: 7, SEQ ID NO: 8, or SEQ ID NO: 9.

11. The method of claim 1, wherein the increase or the decrease in the amount of the cell population is determined by a method performed in vitro using at least one antibody against a cell marker of CCR9+ FoxP3+ T cells, CCR9+ IFN-gamma+ T cells, CCR9+ IL17A+ T cells, FoxP3+ T cells, IFN-gamma+ T cells, and/or IL17A+ T cells.

12. A method of treating Inflammatory Bowel Disease (IBD) in a subject in need thereof, the method comprising:
   administering to the subject an anti-SMAD7 therapy;
   determining the amount of at least one cell population selected from the group consisting of: CCR9+ FoxP3+ T cells, CCR9+ IFN-gamma+ T cells, CCR9+ IL17A+ T cells, FoxP3+ T cells, IFN-gamma+ T cells, and IL17A+ T cells in a sample from the subject; and,
   if after the administering step the subject is determined to have an increase in the amount of the cell population of CCR9+ FoxP3+ cells, and/or a decrease in the amount of at least one of the cell populations of CCR9+

IFN-gamma+ T cells, CCR9+ IL17A+ T cells, FoxP3+ T cells, IFN-gamma+ T cells, and IL17A+ T cells, in at least one sample obtained from the subject relative to a known control level of the corresponding cell population, then continuing the anti-SMAD7 therapy.

13. The method of claim 12, wherein the subject is determined to have two or more of the following:
an increase in the amount of CCR9+ FoxP3+ T cells that indicates that the subject is likely to respond, or is responsive, to the anti-SMAD7 therapy;
a decrease in the amount of CCR9+ IFN-gamma+ T cells that indicates that the subject is likely to respond, or is responsive, to the anti-SMAD7 therapy;
a decrease in the amount of CCR9+ IL17A+ T cells that indicates that the subject is likely to respond, or is responsive, to the anti-SMAD7 therapy;
a decrease in the amount of FoxP3+ T cells that indicates that the subject is likely to respond, or is responsive, to the anti-SMAD7 therapy;
a decrease in the amount of IFN-gamma+ T cells that indicates that the subject is likely to respond, or is responsive, to the anti-SMAD7 therapy;
a decrease in the amount of IL17A+ T cells that indicates that the subject is likely to respond, or is responsive, to the anti-SMAD7 therapy.

14. The method of claim 12, wherein the increase or the decrease in the amount of the cell population is determined by a method carried out in vitro.

15. The method of claim 12, wherein the Inflammatory Bowel Disease (IBD) is Crohn's disease (CD) and/or ulcerative colitis (UC).

16. The method of claim 12, wherein the increase in the amount of CCR9+ FoxP3+ T cells, and/or the decrease in the amount of CCR9+ IFN-gamma+ T cells, the decrease in the amount of CCR9+ IL17A+ T cells, the decrease in the amount of FoxP3+ T cells, the decrease in the amount of IFN-gamma+ T cells, or the decrease in the amount of IL17A+ T cells indicates that the subject is likely to enter remission.

17. The method of claim 12, wherein the increase or the decrease in the amount of the cell population is determined by flow cytometry, by immunohistochemistry, and/or by RNA/DNA analysis.

18. The method of claim 17, wherein flow cytometry and/or the immunohistochemistry is performed using an antibody selected from the group consisting of: an anti-CCR9 antibody, an anti-FoxP3 antibody, an anti-IFN-gamma antibody, and an anti-IL17A antibody.

19. The method of claim 12, wherein the control level is a baseline level of the corresponding cell population obtained from the subject prior to administration of the anti-SMAD7 therapy, or obtained immediately after the administration of the anti-SMAD7 therapy.

20. The method of claim 19, wherein the anti-SMAD7 therapy is an anti-SMAD7 antisense therapy.

21. The method of claim 20, wherein the anti-SMAD7 antisense therapy is an anti-SMAD7 antisense oligonucleotide comprising the antisense oligonucleotide sequence of SEQ ID NO: 4, SEQ ID NO: 5, SEQ ID NO: 6, SEQ ID NO: 7, SEQ ID NO: 8, or SEQ ID NO: 9.

22. The method of claim 12, wherein the at least one sample is a blood sample or a tissue sample.

23. The method of claim 22, wherein the tissue sample is from the gastrointestinal tract of the subject.

24. The method of claim 12, wherein the subject is being administered the anti-SMAD7 therapy when the at least one sample is obtained.

* * * * *